United States Patent [19]

Harrison et al.

[11] Patent Number: 5,728,695
[45] Date of Patent: Mar. 17, 1998

[54] SPIROKETAL DERIVATIVES, COMPOSITIONS CONTAINING THEM AND THEIR USE AS THERAPEUTIC AGENTS

[75] Inventors: Timothy Harrison, Great Dunmow; Simon Neil Owen, Leyton; Eileen Mary Seward, Bishop Stortford; Christopher John Swain, Cambridge, all of United Kingdom

[73] Assignee: Merck Sharp & Dohme Limited, Hoddesdon, England

[21] Appl. No.: 849,969

[22] PCT Filed: Dec. 15, 1995

[86] PCT No.: PCT/GB95/02927

§ 371 Date: Jun. 20, 1997

§ 102(e) Date: Jun. 20, 1997

[87] PCT Pub. No.: WO96/20197

PCT Pub. Date: Jul. 4, 1996

[30] Foreign Application Priority Data

Dec. 23, 1994 [GB] United Kingdom ............... 9426103

[51] Int. Cl.⁶ ..................... A61K 31/535; C07D 498/10
[52] U.S. Cl. .......................... 514/230.8; 544/71
[58] Field of Search ........................ 544/71; 514/230.8

[56] References Cited

FOREIGN PATENT DOCUMENTS 0 577 394  1/1994  European Pat. Off. .

OTHER PUBLICATIONS

C. Amsterdamsky, et al., *Tetrahedron Letters*, vol. 22, No. 15, 1981, pp. 1403–1406.

R.E. Lutz, et al., *Journal of Organic Chemistry*, vol. 25, 1960, pp. 928–931.

*Primary Examiner*—Robert W. Ramsuer
*Attorney, Agent, or Firm*—J. Eric Thies; David L. Rose

[57] ABSTRACT

The present invention relates to spiroketal derivatives of formula (I) and pharmaceutically acceptable salts thereof wherein $R^1$, $R^2$, $R^3$, $R^4$, $R^5$, $R^6$, $R^{9a}$, $R^{9b}$, m and n are as defined in the specification, and to processes for their preparation, to intermediates used in their synthesis, to pharmaceutical compositions containing them, and to their use in therapy. The compounds are of particular use in the treatment or prevention of pain, inflammation, migraine, emesis and postherpetic neuralgia.

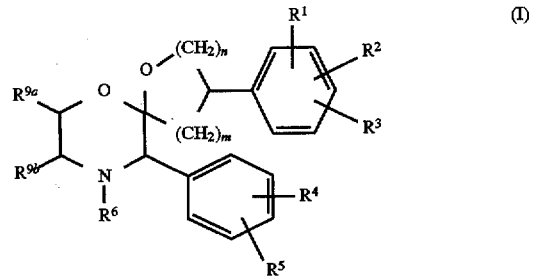

28 Claims, No Drawings

SPIROKETAL DERIVATIVES, COMPOSITIONS CONTAINING THEM AND THEIR USE AS THERAPEUTIC AGENTS

This application is a 371 of PCT GB 95/02927 filed Dec. 23, 1995, published as WO96/20197 Jul. 4, 1996.

This invention relates to a class of spiroketal compounds which are useful as tachykinin antagonists. The present invention also relates to processes for their preparation, pharmaceutical compositions containing them, and to their use in therapy.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, Peptides (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystisis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (1987) 8, 506–510], specifically in the transmission of pain in migraine (B. E. B. Sandberg et al, J. Med Chem, (1982) 25, 1009) and in arthritis [Levine et al Science (1984) 226, 547–549]. Tachykinins have also been implicated in gastrointestinal (GI) disorders and diseases of the GI tract such as inflammatory bowel disease [Mantyh et al Neuroscience (1988) 25(3), 817–37 and D. Regoli in "Trends in Cluster Headache" Ed. Sicuteri et al Elsevier Scientific Publishers, Amsterdam (1987) page 85)] and emesis [F. D. Tattersall et al, Eur. J. Pharmacol., (1993) 250, R5–R6]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al, "Neuropeptides in Synovium of Patients with Rheumatoid Arthritis and Osteoarthritis" in J. Rheumatol. (1988) 15(12), 1807–10]. Therefore, substance P is believed to be involved in the inflammatory response in diseases such as rheumatoid arthritis and osteoarthritis, and fibrositis [O'Byrne et at, Arthritis and Rheumatism (1990) 33, 1023–8]. Other disease areas where tachykinin antagonists are believed to be useful are allergic conditions [Hamelet et al, Can. J. Pharmacol. Physiol. (1988)66, 1361–7], immunoregulation [Lotz et al, Science (1988) 241, 1218–21 and Kimball et al, J. Immunol. (1988) 141(10), 3564–9] vasodilation, bronchospasm, reflex or neuronal control of the viscera [Mantyh et al, PNAS (1988) 85, 3235–9] and, possibly by arresting or slowing β-amyloid-mediated neurodegenerative changes [Yankner et al, Science (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, Cancer Research (1992) 52, 4554–7].

Substance P may also play a role in demyelinating diseases such as multiple sclerosis and amyotrophic lateral sclerosis [J. Luber-Narod et al, poster C.I.N.P. XVIIIth Congress, 28th Jun.–2nd Jul. 1992], and in disorders of bladder function such as bladder detrusor hyper-reflexia (Lancet, 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

European patent specification no. 0 577 394 (published 5th Jan. 1994) discloses morpholine and thiomorpholine tachykinin receptor antagonists of the general formula

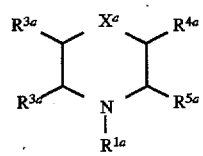

wherein $R^{1a}$ is a large variety of substituents;

$R^{2a}$ and $R^{3a}$ are inter alia hydrogen;

$R^{4a}$ is inter alia

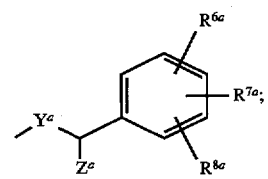

$R^{5a}$ is inter alia optionally substituted phenyl;

$R^{6a}$, $R^{7a}$ and $R^{8a}$ are a variety of substituents;

$X^a$ is O, S, SO or $SO_2$;

$Y^a$ is inter alia O; and $Z^a$ is hydrogen or $C_{1-4}$alkyl.

We have now found a further class of non-peptides which are potent antagonists of tachykinins, especially of substance P.

The present invention provides compounds of the formula (I):

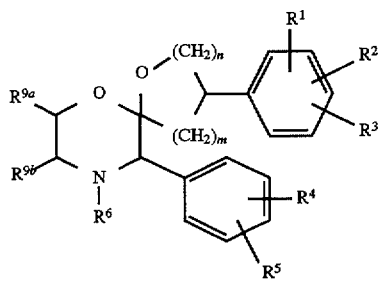

wherein $R^1$ represents hydrogen, halogen, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, $C_{1-6}$alkoxy, fluoro$C_{1-6}$alkyl, fluoro$C_{1-6}$alkoxy, $C_{1-4}$alkyl substituted by a $C_{1-4}$alkoxy or hydroxy group, hydroxy, trimethylsilyl, nitro, CN, $SR^a$, $SOR^a$, $SO_2R^a$, $COR^a$, $CO_2R^a$, $CONR^aR^b$, $NR^aR^b$, $SO_2NR^aR^b$, or $OC_{1-4}$-alkyl$NR^{al\,Rb}$, where $R^a$ and $R^b$ are each independently hydrogen or $C_{1-4}$alkyl;

$R^2$ and $R^3$ each independently represent hydrogen, halogen, $C_{1-6}$alkyl, $C_{1-6}$alkoxy substituted by $C_{1-4}$alkoxy or trifluoromethyl;

or, where $R^1$ and $R^2$ are attached to adjacent carbon atoms, they may be joined such that, together with the carbon atoms to which they are attached, there is formed a 5- or 6-membered ring optionally containing 1 or 2 heteroatoms selected from oxygen, sulfur or nitrogen, or 1 or 2 groups selected from S(O), S(O)$_2$ and $NR^a$, which ring may also contain 1 or 2 double bonds, where $R^a$ is as previously defined;

$R^4$ represents hydrogen, halogen, $C_{1-6}$alkyl, $C_{2-6}$alkenyl, $C_{2-6}$-alkynyl, $C_{3-7}$cycloalkyl, $C_{3-7}$cycloalkyl$C_{1-4}$alkyl, $C_{1-6}$alkoxy, $C_{1-4}$alkyl substituted by a $C_{1-4}$alkoxy group, trifluoromethyl, nitro, CN, $SR^a$, $SOR^a$, $SO_2R^a$, $COR^a$, $CO_2R^a$, $CONR^aR^b$ where $R^a$ and $R^b$ are as previously defined;

$R^5$ represents hydrogen, halogen, $C_{1-6}$alkyl, $C_{1-6}$alkoxy substituted by $C_{1-4}$alkoxy or trifluoromethyl;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, C(NOH)$NR^aR^b$, CONHphenyl($C_{1-4}$alkyl), $COCO_2R^a$, $CONHNR^aR^b$, C(S)$NR^aR^b$, $CONR^aC_{1-6}$alkyl$R^{12}$, $CONR^{13}C_{2-6}$alkenyl, $CONR^{13}C_{2-6}$alkynyl, $COCONR^aR^b$, $CONR^aC(NR^b)$ $NR^aR^b$, $CONR^a$heteroaryl, and phenyl optionally substituted by one, two or three substituents selected from $C_{1-6}$alkyl, $C_{1-6}$alkoxy, halogen and trifluoromethyl) or $C_{1-6}$alkyl, optionally substituted by oxo, substituted by a 5-membered or 6-membered heterocyclic ring containing 2 or 3 nitrogen atoms optionally substituted by =O or =S and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom; $R^{9a}$ and $R^{9b}$ each independently represent hydrogen or $C_{1-4}$alkyl, or $R^{9a}$ and $R^{9b}$ are joined so, together with the carbon atoms to which they are attached, there is formed a $C_{5-7}$ ring;

$R^{12}$ represents $OR^a$, $CONR_aR^b$ or heteroaryl;

$R^{13}$ represents H or $C_{1-6}$alkyl;

m is zero, 1, 2 or 3; and n is zero, 1, 2 or 3; with the proviso that the sum total of m and n is 2 or 3;

and pharmaceutically acceptable salts thereof.

A preferred class of compound of formula (I) is that wherein $R^1$ represents hydrogen, halogen, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, $C_{1-6}$alkoxy, $C_{1-4}$alkyl substituted by a $C_{1-4}$alkoxy group, $OCF_3$, hydroxy, trifluoromethyl, trimethylsilyl, nitro, CN, $SR^a$, $SOR^a$, $SO_2R^a$, $COR^a$, $CO_2R^a$, $CONR^aR^b$ where $R^a$ and $R^b$ are each independently hydrogen or $C_{1-4}$alkyl; and $R^2$ and $R^3$ each independently represent hydrogen, halogen, $C_{1-6}$alkyl, $C_{1-6}$alkoxy substituted by $C_{1-4}$alkoxy or trifluoromethyl.

Certain particularly apt compounds of the present invention include those wherein $R^1$ is hydrogen, $C_{1-4}$alkyl, $C_{1-4}$alkoxy, halo or $CF_3$.

Most aptly $R^2$ is hydrogen, $C_{1-4}$alkyl, $C_{1-4}$alkoxy, halogen or $CF_3$.

Most aptly $R^3$ is hydrogen, fluorine, chlorine or $CF_3$.

Favourably $R^1$ is $C_{1-4}$alkoxy, especially methoxy, ethoxy, n-propoxy, i-propoxy or t-butoxy.

Favourably $R^2$ is hydrogen, fluorine, chlorine or $C_{1-4}$alkyl, especially hydrogen, fluorine, i-propyl, or t-butyl.

Favourably $R^3$ is hydrogen.

Preferably $R^1$ is in the 2-position on the phenyl ring.

Preferably $R^2$ is in the 5-position on the phenyl ring.

Most aptly $R^4$ is hydrogen.

Most aptly $R^5$ is hydrogen, fluorine, chlorine or $CF_3$.

Preferably $R^4$ is hydrogen and $R^5$ is hydrogen or 4-fluoro.

Most aptly $R^{9a}$ and $R^{9b}$ are each independently hydrogen or methyl.

Preferably $R^{9a}$ is hydrogen. Preferably $R^{9b}$ is hydrogen. Most preferably $R^{9a}$ and $R^{9b}$ are both hydrogen.

Preferably n is 1.

Preferably m is 1 or 2, especially 1.

Favourably $R^6$ is $C_{1-6}$alkyl, in particular $CH_2$, $CH(CH_3)$ and $CH_2CH_2$ and especially $CH_2$, substituted by a 5-membered ring.

In particular, the 5-membered ring is a heterocyclic ring selected from:

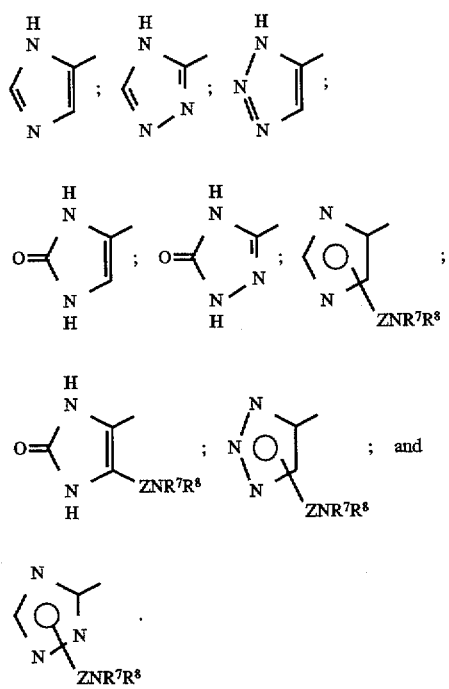

Particularly preferred heterocyclic rings are selected from:

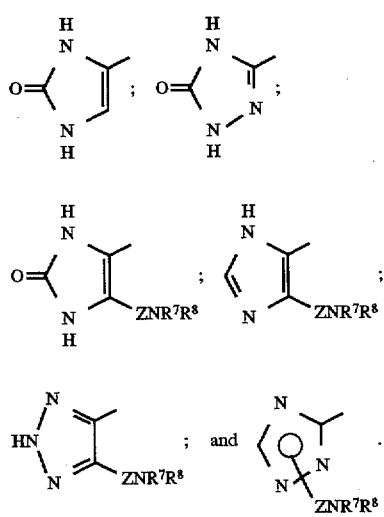

Most especially, the heterocyclic ring is selected from:

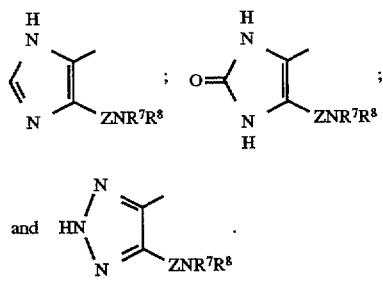

A particularly preferred heterocyclic ring is:

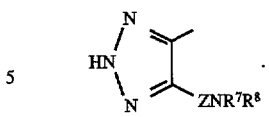

One favoured group of compounds of the present invention are of the formula (Ia) and pharmaceutically acceptable salts thereof:

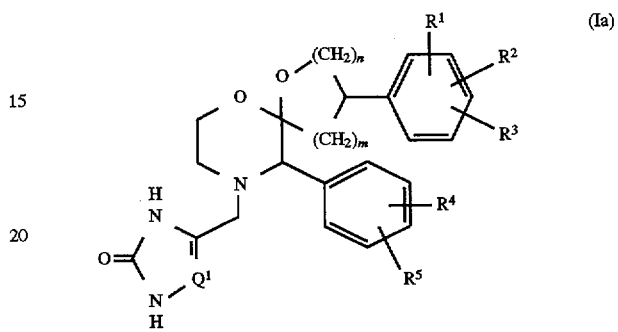

wherein $R^1, R^2, R^3, R^4, R^5$, m and n are as defined in relation to formula (I) and $Q^1$ is CH, N or C—$ZNR^7R^8$ wherein Z, $R^7$ and $R^8$ are as defined in relation to formula (I).

Another favoured group of compounds of the present invention are of the formula (Ib) and pharmaceutically acceptable salts thereof:

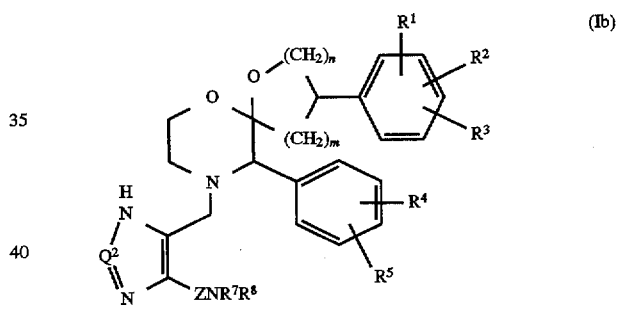

wherein $R^1, R^2, R^3, R^4, R^5$, m and n are defined in relation to formula (I), $Q^2$ is CH or N and Z, $R^7$ and $R^8$ are as defined in relation to formula (I).

A further favoured group of compounds of the present invention are of the formula (Ic) and pharmaceutically acceptable salts thereof:

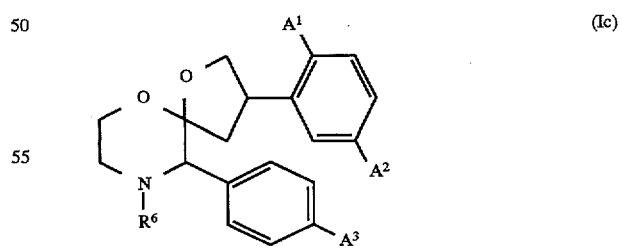

wherein $R^6$ is as defined in relation to formula (I);
$A^1$ is $C_{1-4}$alkoxy;
$A^2$ is hydrogen, halogen, $C_{1-4}$alkyl or fluoro$C_{1-4}$alkyl; and
$A^3$ is hydrogen or halogen.

In particular, $A^1$ is preferably methoxy, ethoxy, n-propoxy or i-propoxy.
In particular $A^2$ is hydrogen, fluorine or trifluoromethyl.
In particular $A^3$ is hydrogen or fluorine.

With respect to compounds of the formulae (I), (Ia), (Ib) and (Ic), Z (where present), may be a linear, branched or cyclic group. Favourably Z contains 1 to 4 carbon atoms and most favourably 1 or 2 carbon atoms. A particularly favourable group Z is $CH_2$.

With respect to compounds of the formulae (I), (Ia), (Ib) and (Ic), $R^7$ may aptly be a $C_{1-4}$alkyl group or a $C_{2-4}$alkyl group substituted by a hydroxyl or $C_{1-2}$alkoxy group, $R^8$ may aptly be a $C_{1-4}$alkyl group or a $C_{1-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

Particularly suitable moieties $ZNR^7R^8$ include those wherein Z is $CH_2$ or $CH_2CH_2$ and $NR^7R^8$ is amino, methylamino, dimethylamino, diethylamino, azetidinyl, pyrrolidino and morpholino.

Further preferred moieties represented by $ZNR^7R^8$ are those wherein Z is $CH_2$ or $CH_2CH_2$, $R^7$ represents hydrogen, $C_{1-4}$alkyl or $C_{3-6}$cycloalkyl and $R^8$ is $C_{2-4}$alkyl substituted by one or two substituents selected from hydroxy, $C_{1-2}$alkoxy, azetidinyl, pyrrolidino, piperidino, morpholino or thiomorpholino.

In particular, Z is preferably $CH_2$ and $NR^7R^8$ is preferably dimethylamino, azetidinyl or pyrrolidino, especially dimethylamino.

Where $R^1$ and $R^2$, together with the carbon atoms to which they are attached, form a 5- or 6-membered ring optionally containing 1 or 2 heteroatoms selected from oxygen, sulfur or nitrogen, or 1 or 2 groups selected from S(O), $S(O)_2$ and $NR^a$, and which ring may also contain 1 or 2 double bonds, it will be appreciated that the ring thus formed may be saturated, partially saturated or unsaturated. Thus, $R^1$ and $R^2$ may represent, for example, —$OCH_2CH_2CH_2$—, —$OCH_2CH_2$—, —$OCH_2CH_2$—, —$OCH_2O$—, —$NR^aCH_2CH_2CH_2$—, —$NR^aCH_2CH_2$—, —$CH_2CH_2CH_2CH_2$—, —$CH_2CH_2CH_2$—, —CH=CH—CH=CH—, —O—CH=CH—, —$NR^a$—CH=CH—, —S—CH=CH—, —$NR^a$—CH=N—, —O—CH=N—, —S—CH=N—, —N=CH—CH=CH—, —CH=N—CH=CH—. Particularly preferred linkages formed by $R^1$ and $R^2$ include , —$OCH_2CH_2CH_2$—, —$OCH_2CH_2CH_2O$—, —$OCH_2CH_2$—, —$OCH_2O$—, —$NR^aCH_2CH_2CH_2$— and —CH=CH—CH=CH—. In these examples, $R^a$ preferably represents a hydrogen atom.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the terms "fluoro$C_{1-6}$alkyl" and "fluoro$C_{1-6}$alkoxy" means a $C_{1-6}$alkyl or $C_{1-6}$alkoxy group in which one or more (in particular, 1 to 3) hydrogen atoms have been replaced by a fluorine atom. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$ and $OCF_3$.

When used herein the term halogen means fluorine, chlorine, bromine and iodine. The most apt halogens are fluorine and chlorine of which fluorine is preferred.

Specific compounds within the scope of this invention include:

(2S,3S,9R)-4-aza-1,7-dioxa-3,9-diphenylspiro[5.5]undecane;

(2S,3S,9S)-4-aza-1,7-dioxa-3,9-diphenyl-spiro[5,5]undecane;

(2R,3S,9S)-4-aza-4-benzyl-1,7-dioxa-3,9-diphenyl-spiro[5.5]undecane;

(2R,3S,9R)-4-aza-4-benzyl-1,7-dioxa-3,9-diphenyl-spiro[5.5]undecane;

(2S,3S,9S)-4-aza-1,7-dioxa-3,9-diphenyl-spiro[5.5]undecane-4-ylmethyl)-2,4-dihydro-1,2,4-triazol-3-one;

4-aza-4-benzyl-1,7-dioxa-3,8-diphenyl-spiro[5.4]decane; and pharmaceutically acceptable salts thereof.

Further specific compounds within the scope of the present invention include:

(2S,3S,9S)-4-aza-1,7-dioxa-3-(4-fluorophenyl)-9-phenylspiro[5.4]decane;

(2S,3S,9S)-4-aza-1,7-dioxa-3-(4-fluorophenyl)-9-(2-methoxyphenyl)spiro [5.4]decane;

(2R,3S,8R)-4-aza-4-benzyl-1,7-dioxa-3-(4-fluorophenyl)-8-phenyl-spiro[5.4]decane;

(2R,3S,8S)-4-aza-4-benzyl-1,7-dioxa-3-(4-fluorophenyl)-8-phenyl-spiro[5.4]decane;

(2R,3S,8R)-4-aza-1,7-dioxa-3-(4-fluorophenyl)-8-phenyl-spiro[5.4]decane;

(2R,3S,9S)-4-aza-1,7-dioxa-3-(4-fluorophenyl)-8-phenyl-spiro[5.4]decane;

(2R,3S,8R)-4-aza-4-(2,3-dihydro-3-oxo-1,2,4-triazol-5-yl)methyl-1,7-dioxa-3-(4-fluorophenyl)-8-phenyl-spiro[5.4]decane;

(2R,3S,8S)-4-aza-4-(2,3-dihydro-3-oxo-1,2,4-triazol-5-yl)methyl-1,7-dioxa-3-(4-fluorophenyl)-8-phenyl-spiro[5.4]decane;

4-aza-4-benzyl-7-dioxa-5-phenyl-9-(2-trifluoromethylphenyl)spiro[5.5]undecane;

(2S,3S,9S)-4-aza-1,7-dioxa-3-(4-fluorophenyl)-9-(2-trifluoromethylphenyl)spiro[5.5]undecane;

(3R,3S,9S)-4-aza-1,7-dioxa-3-(4-fluorophenyl)-9-(2-trifluoromethylphenyl)spiro[5.5]undecane;

(2R,3S,9R)-4-aza-1,7-dioxa-3-(4-fluorophenyl)-9-(2-(trifluoromethyl)phenyl)spiro[5.5]undecane;

(2S,3S,9R)-4-aza-1,7-dioxa-3-(4-fluorophenyl)-9-(2-(trifluoromethyl)phenyl)spiro[5.5]undecane;

(2S,3S,9S)-4-aza-4-(5-(dimethylaminomethyl)-1,2,3-triazol-4-yl)methyl-1,7-dioxa-3-(4-fluorophenyl)-9-(2-(trifluoromethyl)phenyl)spiro[5.5]undecane;

4-aza-4-benzyl-1,7-dioxa-3-(4-fluorophenyl)-9-(3-(trifluoromethyl)phenyl)spiro[5.5]undecane;

(2R,3S,9S)-4-aza-1,7-dioxa-3-(4-fluorophenyl)-9-(3-(trifluoromethyl)phenyl)spiro[5.5]undecane;

(2R,3S,9R)-4-aza-1,7-dioxa-3-(4-fluorophenyl)-9-(3-(trifluoromethyl)phenyl)spiro[5.5]undecane;

(2S,3S,9S)-4-aza-1,7-dioxa-3-(4-fluorophenyl)-9-(3-(trifluoromethyl)phenyl)spiro[5.5]undecane;

(2S,3S,9S)-4-aza-1,7-dioxa-3-(4-fluorophenyl)-9-(3-(trifluoromethyl)phenyl)spiro[5.5]undecane;

(2S,3S,9S)-4-aza-4-(5-(dimethylaminomethyl)-1,2,3-triazol-4-yl)methyl-1,7dioxa-3-(4-fluorophenyl)-9-(3-(trifluoromethyl)phenyl)spiro[5.5]undecane;

(2S,3S,9S)-4-aza-4-benzyl-7-dioxa-5-phenyl-9-(2-(trifluoromethoxy)phenyl)-spiro[5.5]undecane;

(2S,3S,9S)-4-aza-1,7-dioxa-3-(4-fluorophenyl)-9-(2-(trifluoromethoxy)phenyl)spiro[5.5]undecane;

4-aza-1,7-dioxa-3-(4-fluorophenyl)-9-(2-(trifluoromethoxy)phenyl)spiro[5.5]undecane;

(2S,3S,9S)-4-aza-4-(5-(dimethylaminomethyl)-1,2,3-triazol-4-yl)methyl-1,7-dioxa-3-(4-fluorophenyl)-9-(2-(trifluoromethoxy)phenyl)spiro[5.5]undecane;

(2S,3S,9S)-4-aza-4-(2,3-dihydro-3-oxo-1,2,4-triazol-5-yl)methyl-1,7-dioxa-3-(4-fluorophenyl)-9-(3-(trifluoromethyl)phenyl)spiro[5.4]decane;

(2S,3S,9S)-4-aza-1,7-dioxa-3-(4-fluorophenyl)-9-(2-naphthyl)spiro[5.4]decane;

(2S,3S,9S)-4-aza-4-(2,3-dihydro-3-oxo-1,2,4-triazol-5-yl)methyl-1,7-dioxa-3-(4-fluorophenyl)-9-(2-naphthyl)spiro[5.4]decane;

(2S,3S,9S)-4-aza-4-benzyl-1,7-dioxa-3-(4-fluorophenyl)-9-(2-thiomethylphenyl)spiro[5.4]decane;

(2S,3S,9S)-4-aza-1,7-dioxa-9-(5-fluoro-2-methoxyphenyl)-3-(4-fluorophenyl)-4-(1,3-imidazol-4-ylmethyl)spiro[5.4]decane;

(2S,3S,9S)-4-aza-1,7-dioxa-9-(5-fluoro-2-isopropoxyphenyl)-3-(4-fluorophenyl)-4-(1,3-imidazol-4-ylmethyl)spiro[5.4]decane;

(2S,3S,9S)-4-aza-4-benzyl-9-(2,5-dimethoxyphenyl)-1,7-dioxa-3-(4-fluorophenyl)spiro[5.4]decane;

(2S,3S,9S)-4-aza-4-(carbonylmethylpyrrolidin-1-yl)-1,7-dioxa-3-(4-fluorophenyl)spiro[5.4]decane;

and pharmaceutically acceptable salts thereof.

Yet further specific compounds within the scope of the present invention include those compounds listed in Tables 1 and 2 and pharmaceutically acceptable salts thereof.

In a further aspect of the present invention, the compounds of formula (I) will preferably be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I), (Ia), (Ib) and (Ic) will have the preferred stereochemistry of the 3-position that is possessed by the compound of Example 1 (i.e. 3-(S)). Thus for example as shown in formula (Id)

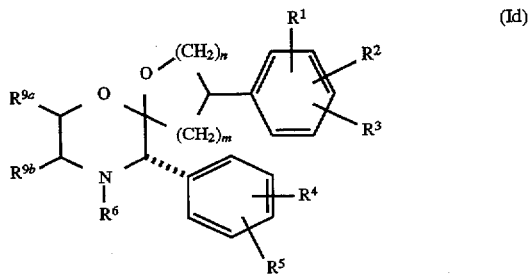

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, nonionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 µm, particularly 0.1 and 0.5 µm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla. USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-$HT_3$ antagonist, such as ondansetron, granisetron or tropisetron, or other anti-emetic medicaments, for example, a dopamine antagonist such as metoclopramide. Additionally, a compound of formula (I) may be administered in combination with an anti-inflammatory corticosteroid, such as dexamethasone. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5–R6, the compounds of the present invention were found to attenuate the retching and vomiting induced by cisplatin.

The compounds of formula (I) are also particularly useful m the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (i) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), the compounds according to the invention may be prepared from a compound of formula (I) in which $R^6$ is H, hereinafter referred to as compounds of formula (II)

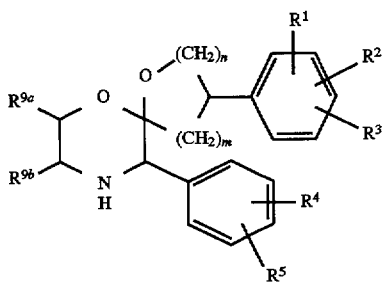

wherein $R^1$, $R^2$, $R^3$, $R^4$, $R^5$, $R^{9a}$, $R^{9b}$, m and n are as defined in relation to formula (I) by reaction with a compound of formula (III):

where $R^{6a}$ is a group of the formula $R^6$ as defined in relation to formula (I) or a precursor therefor and LG is a leaving group such as an alkyl- or arylsulphonyloxy group (e.g. mesylate or tosylate) or a halogen atom (e.g. bromine, chlorine or iodine); and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

According to another process (B), compounds of formula (I) wherein $R^6$ represents a 1,2,3-triazol-4-ylmethyl group substituted by $CH_2NR^7R^8$, may be prepared by reaction of a compound of formula (IV)

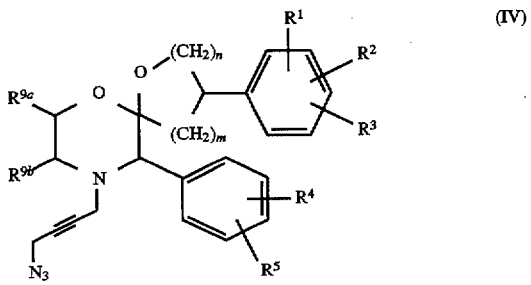

with an amine of formula $NHR^7R^8$, in a suitable solvent such as an ether, for example, dioxan, at elevated temperature, for example, between 50° C. and 100° C., in a sealed tube, or the like. This reaction is based upon that described in *Chemische Berichte* (1989) 122, p. 1963.

According to a further process (C), compounds of formula (I) wherein $R^6$ represents a $C_{1-6}$alkyl group which is substituted by an unsubstituted or substituted 1,2,4-triazolyl group, may be prepared by reaction of an intermediate of formula (II) with a compound of formula (V)

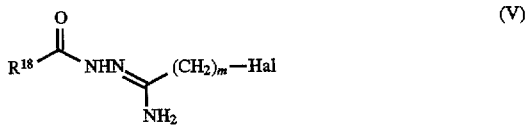

wherein Hal is a halogen atom, for example, bromine, chlorine or iodine, m is an integer from 1 to 6 and $R^{18}$ is H, $CONH_2$ or $OCH_3$ (which is converted to an oxo substituent under the reaction conditions), in the presence of a base, followed where necessary by conversion to a compound of formula (I), for example, by reduction of the $CONH_2$ group to $CH_2NH_2$.

Suitable bases of use in the reaction include alkali metal carbonates such as, for example, potassium carbonate. The reaction is conveniently effected in an anhydrous organic solvent such as, for example, anhydrous dimethylformamide, preferably at elevated temperature, such as about 140° C.

A suitable reducing agent for the group $CONH_2$ is lithium aluminium hydride, used at between −10° C. and room temperature.

According to another process, (D), compounds of formula (I) may be prepared from intermediates of formula (VI)

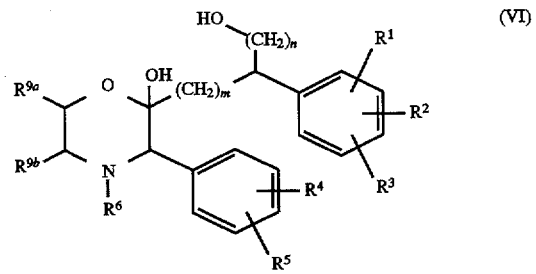

by an acid catalysed intramolecular cyclisation reaction.

Suitable acids of use in the reaction include mineral acids such as, for example, hydrochloric acid. The reaction is conveniently effected in a suitable organic solvent, such as alcohol, e.g. methanol, at elevated temperature, for example, at the reflux temperature of the chosen solvent.

Further details of suitable procedures will be found in the accompanying Examples.

According to a further process (E), compounds of formula (I) may also be prepared from other compounds of formula (I) using suitable interconversion procedures. In particular, interconversion processes may be used to vary the group $R^6$. For example, compounds of formula (I) wherein $R^6$ is other than H may be prepared from the corresponding compounds of formula (I) wherein $R^6$ is H by reaction with a reagent suitable to introduce the group $R^6$, for example, compounds of formula (I) wherein $R^6$ is $COR^a$ may be prepared from compounds of formula (I) wherein $R^6$ is H by, for example, reaction with an appropriate acid anhydride.

Compounds of formula (I) wherein $R^6$ is $C_{1-6}$alkyl may be prepared from corresponding compounds of formula (I) wherein $R^6$ is $COR^a$ by reduction using, for example, borane or a borohydride such as sodium cyanoborohydride.

Compounds of formula (I) wherein $R^6$ is $C_{1-6}$alkyl substituted by $CONR^aR^b$ may be prepared from corresponding compounds of formula (I) wherein $R^6$ is $C_{1-6}$alkyl substituted by $CO_2R^a$ by treatment with ammonia or an amine of formula $NR^aR^b$.

Compounds of formula (I) wherein $R^6$ is $C_{1-6}$alkyl substituted by 5-oxadiazolyl may be prepared from compounds of formula (I) wherein $R^6$ is $C_{1-6}$alkyl substituted by $CO_2R^a$, where $R^a$ represents $C_{1-6}$alkyl, by reaction with a compound of formula (VII)

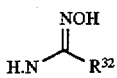 (VII)

wherein $R^{32}$ represents H or a suitable substituent, in the presence of a base.

Suitable bases of use in the reaction include alkali metals, such as, for example, sodium, and alkali metal hydrides, such as, for example, sodium hydride.

The reaction is conveniently effected in a suitable organic solvent. Which solvents will be appropriate will depend on the nature of the base used. For example, where the base used is an alkali metal, suitable solvents will include alcohols, for example, ethanol, whereas where the base used is an alkali hydride, suitable solvents will include ethers, for example, tetrahydrofuran.

Preferably the reaction is conducted at elevated temperature, such as the reflux temperature of the chosen solvent.

Compounds of formula (I) wherein $R^6$ is $C_{1-6}$alkyl substituted by thiazolyl may be prepared from compounds of formula (I) wherein $R^6$ is $C_{1-6}$alkyl substituted by $CSNH_2$ by reaction with a compound of formula Hal—$CH_2C(O)$—$R^{60}$, where Hal is a halogen atom, such as bromine, chlorine or iodine, and $R^{60}$ represents H or a suitable substituent.

Compounds of formula (I) wherein $R^6$ is $C_{1-6}$alkyl substituted by thioxotriazolyl may be prepared from compounds of formula (I) wherein $R^6$ is $C_{1-6}$alkyl substituted by $CONHNH_2$ by reaction with a compound of formula $R^{61}NCS$, wherein $R^{61}$ represents H or a suitable substituent such as $C_{1-6}$alkyl, in the presence of a base.

Suitable bases of use in the reaction include organic bases such as, for example, 1,8-diazabicyclo[5.4.0]undec-7-ene (DBU) The reaction is conveniently effected in a suitable organic solvent, such as alcohol, e.g. butanol.

According to a further general process (F) compounds of formula (I) in which n is 1 and m is 1 or 2, may be prepared by the reduction of a compound of formula (XX)

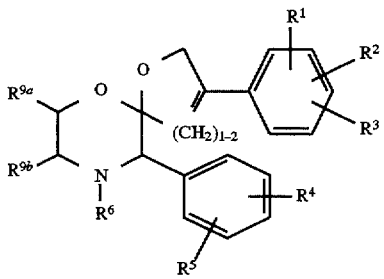 (XX)

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof; borane in tetrahydrofuran; 9-boracyclo[3.3.1]nonane (9-BBN) in an ether such as tetrahydrofuran and lithium triethylborohydride (Super-Hydride™) in an ether such as tetrahydrofuran.

Intermediates of formula (IV) may be prepared from a compound of formula (VIII)

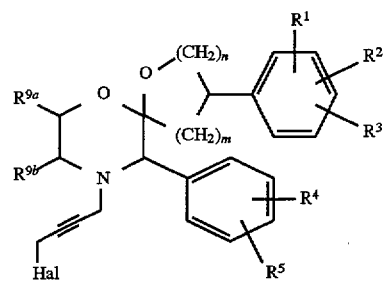 (VIII)

wherein Hal is a halogen atom, for example, chlorine, bromine or iodine, especially chlorine, by reaction with an azide, for example, sodium azide in a suitable solvent such as dimethylsulphoxide at or below room temperature.

Compounds of formula (VIII) may be prepared by a dropwise addition of an intermediate of formula (II) to a dihaloacetylene of formula Hal—$CH_2$—C≡C—$CH_2$—Hal where each Hal is independently chlorine, bromine or iodine, especially chlorine. The reaction is conveniently effected in a suitable solvent such as dimethylformamide in the presence of a base such as potassium carbonate.

Compounds of formula (V) may be prepared as described in *J. Med. Chem.*, (1984) 27,849.

Intermediates of formula (VI) wherein m is 2 may be prepared by the reduction of a compound of formula (IX):

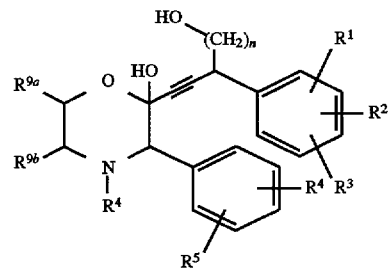 (IX)

or a protected derivative thereof, using conventional methodology, for instance, by catalytic hydrogenation using a metal catalyst such as palladium or platinum or oxides thereof, preferably in a solvent such as an alcohol, e.g. ethanol, or an ester, e.g. ethyl acetate.

Compounds of formula (IX) may be prepared by the reaction of a compound of formula (X):

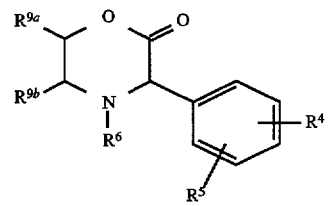 (X)

with compound of formula (XI):

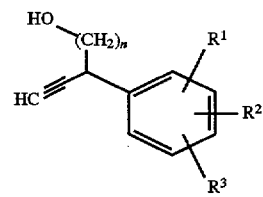 (XI)

or a protected derivative thereof, by lithiation using n-butyl lithium followed by quenching with, for example, sodium dihydrogen orthophosphate. The reaction is conveniently effected in a solvent such as an ether, e.g. tetrahydrofuran, at reduced temperature, for example, at −78° C.

Compounds of formula (X) may be prepared by methods described in European Patent Specification No. 0 577 394-A, or by analogous methods.

Compounds of formula (XI) are known compounds (see *Chemische Berichte*, (1988) 121, 1315–1320) or may be prepared by analogous methods.

For compounds wherein $R^6$ is a $C_{1-6}$alkyl group substituted by a 5-membered heterocycle which in turn is substituted by a $ZNR^7R^8$ group where Z is $CH_2$, certain favoured compounds of formula (I) may be prepared from a corresponding compound with a hydrogen atom in place of the $ZNR_7R^8$. Thus, for example a compound of the formula (I) wherein $R^6$ is an imidazolinone group carrying a $CH_2NR^7R^8$ moiety may be prepared from a corresponding compound lacking the $CH_2NR^7R^8$ moiety by reaction with formaldehyde and an amine $NHR^7R^8$ under conventional Mannich reaction conditions, for example in methanol with heating. If desired a pre-formed reagent such as $R^7R^8N^+=CH_2.I^-$ may be employed and a tertiary amine such as triethylamine used as acid acceptor.

Alternatively a compound of formula (I) wherein $R^6$ is a $C_{1-6}$alkyl group substituted by an imidazolinone group may be reacted with paraformaldehyde and an amine for example a secondary amine such as pyrrolidine or morpholine to give a compound wherein the imidazolinone ring is substituted by $CH_2NR^7R^8$ where $R^7$, $R^8$ and the nitrogen atom to which they are attached form a heteroaliphatic ring of 4 to 7 ring atoms which may optionally contain an oxygen ring atom or a second nitrogen atom which will be part of a NH or $NR^c$ moiety, where $R^c$ is as previously defined.

This reaction may be performed in a conventional manner, for instance, in a suitable solvent such as an alcohol, for example, methanol at an elevated temperature up to the boiling point of the solvent.

A further alternative method for the preparation of certain compounds of formula (I) involves the reaction of an intermediate of formula (II) as defined above with one of the compounds of formula (XII):

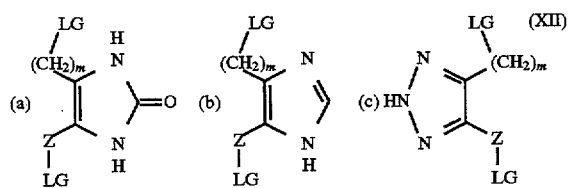

(XII)

wherein each LG, which may be the same or different, is a leaving group, such as an alkyl- or arylsulphonyloxy group (e.g. mesylate or tosylate) or, in particular, a halogen atom, (e.g. bromine, chlorine or iodine), m is an integer from 1 to 6 and X and Z are as defined in formula (I), followed by reaction of the resultant compound with an amine $NHR^7R^8$ to complete the $ZNR^7R^8$ moiety.

This reaction is conveniently effected in an organic solvent such as dimethylformamide in the presence of an acid acceptor such as potassium carbonate.

It will be appreciated that where necessary, reactive groups may be protected, thus for example, the NH groups of an imidazolinone of formula (XIIa) may be protected by any suitable amine protecting group such as an acetyl group.

Compounds of formula (XX) may be prepared by the reaction of a compound of formula (XXI):

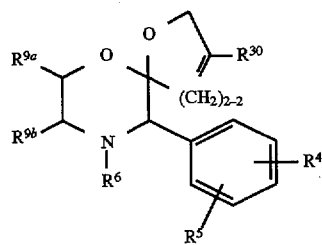

(XXI)

wherein $R^{30}$ is a suitable leaving group such as $—OSO_2CF_3$, with a boronic acid of formula (XXII):

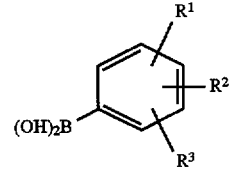

(XXII)

or an ester or an anhydride thereof.

The reaction is preferably effected in the presence of a transition metal catalyst such as tetrakis (triphenylphosphine)palladium (0) in a suitable solvent such as an ether, for example, tetrahydrofuran or 1,2-dimethoxyethane, in the presence or absence of water, or an aromatic hydrocarbon, for example, benzene. The reaction is preferably effected in the presence of a base such as an alkali or alkaline earth metal carbonate, for example, sodium carbonate, at a suitable temperature up to reflux.

Alternatively, compounds of formula (XX) may be prepared by the reaction of a compound of formula (XXIV)

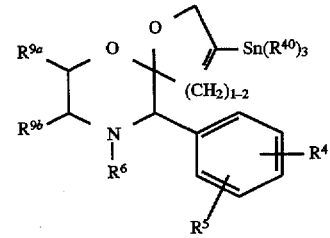

(XXIV)

wherein each $R^{40}$ is a $C_{1-4}$alkyl group, preferably methyl groups, with a compound of formula (XXV)

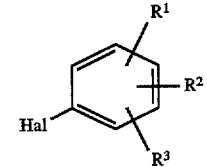

(XXV)

wherein Hal is a halogen atom, for example, chlorine, bromine or iodine, especially bromine.

The reaction is conveniently effected in the presence of lithium chloride and a transition metal catalyst such as triphenylphosphine palladium(0). Suitable solvents for the reaction include aromatic hydrocarbons, for example, toluene, the reaction being effected at a temperature between 80° C. and the reflux temperature of the solvent.

Compounds of formula (XXIV) may be prepared from a corresponding compound of formula (XXI) by reaction with a compound of the formula $(R^{40})_3Sn—Sn(R^{40})_3$, for example, hexamethyl distannane. The reaction is conveniently effected in the presence of a base, for example, lithium carbonate, and a catalyst such as triphenylphosphine palladium(0). Suitable solvents for the reaction include ethers, such as tetrahydrofuran, the reaction being effected at a temperature between room temperature and 100° C., for example, at about 60° C.

Compounds of formula (XXI) may be prepared from a compound of formula (XXIII):

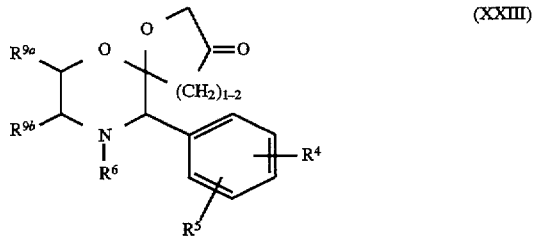

(XXIII)

by enolisation of the ketone in the presence of a base, for example, sodium hexamethyldisilazide, followed by reaction with a reagent capable of introducing a suitable leaving group, for instance, where $R^{30}$ is $-OSO_2CF_3$, using 2-[N, N-bis(trifluoromethylsulphonyl)amino]-5-chloropyridine or triflic anhydride. The reaction is conveniently effected in a suitable solvent such as an ether, for example, tetrahydrofuran at a reduced temperature, for instance, −78° C.

Compounds of formula (XXII) and (XXV) are either known compounds or may be prepared in a conventional manner using standard methodology or methods analogous to those described herein.

Compounds of formula (XXIII) may be prepared from a compound of formula (X) by the reaction sequence of Scheme 1 or by methods analogous thereto:

Scheme 1

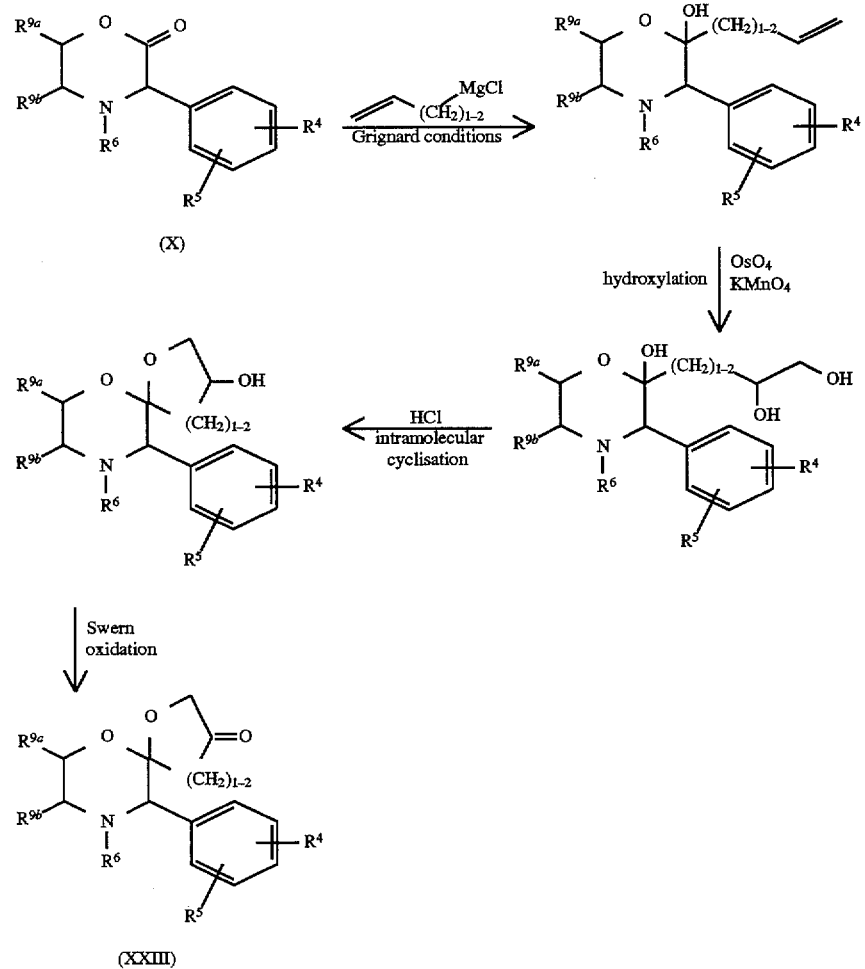

(XXIII)

In a preferred embodiment of the aforementioned processes, $R^6$ is a benzyl group. The reduction reaction described as process (G) above for the preparation of compounds of formula (XX) may conveniently replace the benzyl group with a hydrogen atom. It will be appreciated from the discussion above that compounds of formula (I) wherein $R^6$ is a hydrogen atom are particularly preferred precursors to other compounds of formula (I).

It will be appreciated that compounds of the formula (I) wherein $R^6$ contains an =O or =S substituent can exist in tautomeric forms. All such tautomeric forms and mixtures thereof are included within this invention. Most aptly the =O or =S substituent in $R^6$ is the =O substituent.

Where they are not commercially available, the intermediates of formula (III) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

Further methods suitable for adaptation to the preparation of the spiroketal compounds of the present invention are described by F. Perron and K. F. Albizati in Chem. Rev., (1989) 89, 1617–1661.

The exemplified compounds of this invention were tested by the methods set out at pages 36 to 39 of International Patent Specification No. WO 93/01165. The compounds or, in the case of prodrugs, the parent compounds, were found to be active with $IC_{50}$ at the $NK_1$, receptor of less than 1 μM on said test method.

For the avoidance of doubt, the nomenclature adhered to throughout this specification is based upon the following structures:

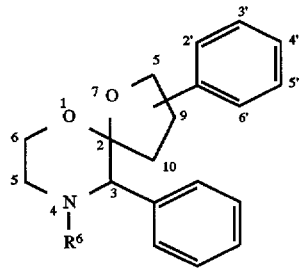

and

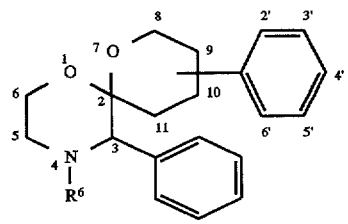

The following non-limiting Examples serve to illustrate the preparation of compounds of the present invention:

DESCRIPTION 1

2-Phenyl-but-3-yn-1-ol

2-Phenyl-4-trimethylsilyl-but-3-yn-1-ol (*Chem. Ber.* (1988), 121, 1315–1320) (7.8 g) was dissolved in ethanol and the solution was cooled to –5° C. A solution of silver nitrate (8.9 g) in ethanol (60 ml) and water (21 ml) was added dropwise to the acetylene solution such that the temperature remained below 5° C. This precipitated the acetylene as the silver complex. A solution of potassium cyanide (17 g) in water (30 ml) was added dropwise to the stirred acetylene mixture and the resulting mixture was stirred at room temperature for 30 minutes. The mixture mainly dissolved and was diluted with water and extracted with ethyl acetate. The organic extracts were washed with brine, dried ($MgSO_4$) and evaporated. The residue was purified on silica using 10% ethyl acetate in hexane as eluant to afford the title compound (5 g) as a colourless oil.

H NMR (360 MHz, $CDCl_3$) δ2.35 (1H, d, J=3 Hz), 3.75–3.83 (2H, m), 3.83–3.91 (1H, m), 7.25–7.43 (5H, m).

DESCRIPTION 2 tert-Butyldimethylsilyloxy-2-phenyl-but-3-yne

The product of Description 1 (5 g) was dissolved in dichloromethane at 0° C. under nitrogen. 2,6-Lutidine (4.8 ml) was added to the solution followed by dropwise addition of tert-butyldimethylsilyl trifluoromethane sulfonate (9.44 ml); the resulting solution was stirred overnight at room temperature. The solution was washed with water (×3), brine and dried ($MgSO_4$) and the solvent was removed in vacuo. The residue was purified on silica using 1–5% diethyl ether in hexane as eluant to afford the title compound as a pale yellow oil (8.8 g). $^1H$ NMR (360 MHz, $CDCl_3$) δ0.36 (6H, s), 0.91 (9H, s), 2.33 (1H, d, J=3 Hz), 3.77–3.81 (1H, dd), 3.82–3.88 (1H, m), 3.91–3.97 (1H, dd), 7.29–7.47 (5H, m).

DESCRIPTION 3

4-Benzyl-2-[4-(tert-butyl-dimethyl-silanyloxy-3-phenyl-but-1-ynyl-3-phenyl-morpholin-2-ol The product of Description 2 (8.8 g) was dissolved in tetrahydrofuran (100 ml, anhydrous) and the solution was cooled to –78° C. n-Butyl lithium (28.8 ml, 1.6M in hexane) was added dropwise such that the internal temperature was maintained below –70° C. The resulting solution was stirred for 1 h. 4-Benzyl-3-(S)-phenyl-2-morpholinone (see European Patent Specification No. 0577394-A) (10.1 g) was dissolved in tetrahydrofuran (50 ml) and was cooled to –78° C. This solution was added dropwise to the acetylide solution and the resulting reaction mixture was stirred at –78° C. for 1 h. The mixture was allowed to warm to 0° C. and was quenched with sodium dihydrogen phosphate (250 ml, 10% aqueous solution). Tetrahydrofuran was removed in vacuo and the residue was extracted into ethyl acetate (×3). The combined organic solution was washed with water and brine, then dried ($MgSO_4$) and concentrated in vacuo. The residue was purified on silica using 5–15% ethyl acetate in hexane as eluant to afford the product as a mixture of inseparable isomers (7.5 g). The yellow oil was not purified further but was taken on to the next step. MS $CI^+$ m/z 528 (M+1$^+$, 100%).

DESCRIPTION 4

4-Benzyl-2-[4-(tert-butyl-dimethyl-silanyloxy)-3-phenyl-butyl]-3-phenyl-morpholin-2-ol The compound described in Description 3 was dissolved in ethyl acetate and a suspension of platinum oxide (500 mg) in ethyl acetate was added. The mixture was hydrogenated at 40 psi for 2 h. The catalyst was removed by filtration and the solvent was removed in vacuo to afford the product as a mixture of isomers. This mixture (7.3 g) was used in the next step without purification. MS CI$^+$ m/z 532 (M+1$^+$, 100%).

DESCRIPTION 5

4-Benzyl-2-(4-hydroxy-3-phenyl-butyl)-3-phenyl-morpholin-2-ol

The silyl ether described in Description 4 (7.3 g) was dissolved in methanol. Methanolic hydrogen chloride (14 ml, 1M) was added followed by Amberlyst catalyst (300 mg). An additional aliquot of methanolic hydrogen chloride was added to the mixture and the reaction mixture was stirred for 2 h. The mixture was filtered and concentrated to yield a yellow oil (5 g). This diol was used in the next reaction without purification. MS CI$^+$ m/z 418 (M+1$^+$, 90%).

DESCRIPTION 6 tert-Butyldimethylsilyloxy-1-phenyl-prop-1-yne

1-Phenyl-2-propyn-1-ol (7 g) was dissolved in dichloromethane at 0° C. under nitrogen. 2,6-Lutidine (6.17 ml) was added to the solution followed by dropwise addition of tert-butyldimethylsilyl trifluoromethane sulfonate (12.16 ml); the resulting solution was stirred overnight at room temperature. The dichloromethane was washed with water (2×), brine and dried (MgSO$_4$) and solvent removed in vacuo. The residue was purified on flash silica using 100% petrol moving to 5% ethyl acetate/petrol, to afford the title compound as a yellow oil (10.31 g).

$^1$H NMR (250 MHz, CDCl$_3$) δ0.18 (3H, s), 0.2 (3H, s), 0.96 (9H, s), 2.55 (1H, d, J=2 Hz), 5.49 (1H, d, J=2 Hz), 7.26–7.40 (3H, m), 7.48–7.53 (2H, m).

DESCRIPTION 7

4-Benzyl -2-[3-tert-butyl-dimethyl-silanyloxy)-3-phenyl-prop-1-ynyl-3-phenyl-morpholin-2-ol The product of Description 6 (5 g) was dissolved in dry THF (40 ml) and cooled to −78° C. n-Butyl lithium (1.6M in hexane; 13.9 ml) was added dropwise and stirred for 1 hour; the colour changed to an orange/red colour. 3-(S)-Phenyl-4-benzyl-2-morpholinone (5.4 g) was dissolved in tetrahydrofuran, cooled to −78° C. and added dropwise to the acetylide. The reaction was stirred overnight. The reaction was quenched with sodium dihydrogen orthophosphate and extracted with ethyl acetate (3×100 ml). The combined organics were washed with brine, dried (MgSO$_4$) and concentrated to afford a brown oil. Purification was carried out on flash silica eluted with 5–15% ethyl acetate in hexane which afforded the title compound. MS CI$^+$ m/z 514 (M+1$^+$, 100%).

DESCRIPTION 8

4-Benzyl-2-[3-(tert-butyl-dimethyl-silanyloxy)-3-phenyl-propyl]-3-phenyl-morpholin-2-ol The silyl ether described in Description 7 (1 g) was dissolved in ethyl acetate (50 ml) and wetted platinium (IV) oxide (200 mg) was added. The reaction was placed under an atmosphere of hydrogen (30 psi) for 1 hour. The catalyst was removed by filtration and the solvent removed in vacuo to afford the title compound. MS CI$^+$ m/z 518 (M+1$^+$, 100%).

DESCRIPTION 9

4-Benzyl-2-(3-hydroxy-3-phenyl-propyl)-3-phenyl-morpholin-2-ol

The saturated silyl ether described in Description 8 (1 g) was dissolved in dry methanol (10 ml), methanol hydrogen chloride (5 ml) and Amberlyst catalyst were added and the reaction was stirred for one hour. The catalyst was removed by filtration and the solvent was removed in vacuo to afford a yellow oil. The oil was dispersed between ethyl acetate and sodium carbonate solution. The organic layer was washed with brine, dried (MgSO$_4$) and the solvent removed in vacuo to afford a yellow oil. Purification was carried out on flash silica eluted with 20–30% ethyl acetate in petrol to give the title compound (0.32 g). MS CI$^+$ m/z 404 (M+1$^+$, 100%).

DESCRIPTION 10

(2R,3S)-4-Benzyl-3-(4-fluorophenyl)-2-hydroxy-2-(prop-2-enyl)morpholine (3S)-4-Benzyl-3-(4-fluorophenyl)-2-morpholinone (13.6 g, 47.6 mmol) was dissolved in anhydrous tetrahydrofuran (200 ml) and cooled to below −70° C. under an inert atmosphere. Allyl magnesium chloride (26.2 ml of a 2.0M solution in tetrahydrofuran; 52.4 mmol) was added dropwise over 15 minutes, maintaining the temperature below −70° C. After 30 minutes, the reaction was quenched by the addition of a saturated solution of ammonium chloride and allowed to warm to room temperature. The resulting suspension was extracted with ethyl acetate (3×100 ml), and the combined organic extracts dried (MgSO$_4$) and concentrated in vacuo to yield the tide compound in ~3:1 mixture of the lactols as a light yellow oil (15.3 g, 98%), which was used without further purification. MS (ES$^+$) m/z 328 (M+1, 22%), 310 (M—OH, 61), 269 (100).

DESCRIPTION 11

(2R,3S)-4-Benzyl-2-(2,3-dihydroxy)propyl-3-(4-fluorophenyl)-2-hydroxymorpholine

The alkene of Description 10 (18.9 g, 57.7 mmol) was stirred with osmium tetroxide (0.2 g, 0.8 mmol) and N-methylmorpholine N-oxide (7.78 g, 66.4 mmol) in a solution of tetrahydrofuran (200 ml), 2-methyl-2-propanol (120 ml) and water (14 ml) for 3 days at room temperature. The resulting black solution was diluted with ethyl acetate (200 ml), water (200 ml) and saturated brine (100 ml), separated and the organic fraction dried (MgSO$_4$) and concentrated in vacuo. The resulting black oil (26 g) was purified by flash silica gel chromatography eluting with 50–100% ethyl acetate in hexane to yield the title compound as a mixture of isomers as a white foam (15.9 g, 76%).

Analysis: C$_{20}$H$_{24}$FNO$_4$.0.5H$_2$O requires C, 64.84; H, 6.82; N, 3.78; Found: C, 65.22; H, 6.74; N, 3.68%

MS (ES$^+$) 362 (M+1, 18%), 344 (M—OH, 100).

DESCRIPTION 12

(2R,3S,9RS)-4-Aza-4-benzyl-1,7-dioxa-3-(4-fluorophenyl)-9-hydroxyspiro[5,4]decane and (2S,3S,9RS)-4-Aza-4-benzyl-1,7-dioxa-3-(4-fluorophenyl)-9-hydroxyspiro[5,4]decane The mixture of triols of Description 11 (15.0 g, 41.5 mmol) was dissolved in hydrochloric acid (200 ml, 6M), and methanol (100 ml) and heated at reflux for 5 hours. The cooled solution was basified with 4N sodium hydroxide solution and extracted with ethyl acetate (3×200 ml). The combined organic extracts were dried (MgSO$_4$) and concentrated in vacuo. The resulting black oil (18 g) was purified by flash silica gel chromatography eluting with 33–66% ethyl acetate in hexane to yield the title compounds as pairs of diasteromers.

Isomer pair A, less polar, an orange gum (7.1 g, 50%). $R_f$ 0.37 (50% ethyl acetate/hexane). $^1$H NMR (360 MHz, CDCl$_3$) δ0.42 (~½H, d, J=10.4 Hz)*, 1.69 (½H, dd, J=13.5, 5.5 Hz), 1.86 (½H, d, J=14.6 Hz), 1.96 (½H, d, J=13.6 Hz), 2.15 (½H, dd, J=14.6, 6.4 Hz), 2.30 (1H, dt, J=12.0, 3.6 Hz), 2.76 (1H, d, J=13.1 Hz), 2.79 (1H, d, J=13.2 Hz), 3.11 (~½H, d, J=11.2 Hz)*, 3.34 (1H, d, J=14.2 Hz), 3.35–3.71 (3H, m), 3.91 (½H, dd, J=9.7, 3.6 Hz), 3.98–4.24 (2½H, m), 7.01 (2×½H, t, J=8.8 Hz), 7.08 (2×½H, t J=8.7 Hz), 7.18–7.29 (5H, m), 7.54 and 7.63 (2H, 2×br s) (* exchanges in D$_2$O); MS (ES$^+$) 344 (M+1, 100%).

Isomer B, more polar, an orange glass (4.3 g, 30%). $R_f$ 0.25 (50% ethyl acetate/hexane). $^1$H NMR (360 MHz, CDCl$_3$) δ0.83 (⅔H, br d)*, 1.64 (⅓H, dd, J=14.0, 5.7 Hz), 1.87 (⅔H, d, J=14.6 Hz), 2.02 (⅓H, J=14.0 Hz), 2.15 (⅔H, dd, J=14.6, 6.6 Hz), 2.32–2.41 (1H, m), 2.74–2.82 (1H, m), 3.03 (⅓H, d, J=11.0 Hz)*, 3.14 (⅔H, d, J=13.7 Hz), 3.17 (⅓H, d, J=13.7 Hz), 3.50 (⅓H, d, J=13.6 Hz), 3.59 (⅔H, d, J=13.7 Hz, 3.66–4.16 (5⅓H, m), 4.33 (⅔H, br s), 7.00–7.09 (2H total, m), 7.21–7.31 (5H, m), 7.41–7.52 (2H total, m) (* exchanges in D$_2$O); MS (ES$^+$) 344 (M+1, 100%).

DESCRIPTION 13

(2R,3S)-4-Aza-4-benzyl-1,7-dioxa-3-(4-fluorophenyl)-9-oxospiro[5.4]decane

Anhydrous dimethylsulphoxide (3.4 ml, 47.8 mmol) dissolved in dichloromethane (10 ml) was added dropwise over 10 minutes to a solution of oxalyl chloride (2.0 ml, 22.9 mmol) dissolved in anhydrous dichloromethane (200 ml) cooled to below −70° C. The temperature was maintained below −60° C. during the addition and the solution stirred for a further 15 minutes at below −70° C. The alcohol isomer pair A of Description 12 (6.57 g, 19.1 mmol) dissolved in dichloromethane (40 ml) was added dropwise over 10 minutes, maintaining the temperature below −70° C. and then stirred at this temperature for one hour. Triethylamine (13.3 ml, 95.5 mmol) was added dropwise over 10 minutes, and the reaction allowed to warm to room temperature. The resulting mixture was washed with dilute sodium bicarbonate solution (0.2M) and water (200 ml) and the organic fraction dried (MgSO$_4$) and concentrated in vacuo (7.9 g). The crude product was purified by flash silica gel chromatography eluting with 14–20% ethyl acetate in hexane to yield the title compound as a pale yellow glass which solidified to a buff coloured solid on standing (5.2 g, 80%).

Analysis: C$_{20}$H$_{20}$FNO$_3$ requires C, 70.37; H, 5.91; N, 4.10; Found: C, 70.29; H, 5.83; N, 4.02%

[α]$^{22}$D=+25.6 (c=1.04, CH$_2$Cl$_2$); $^1$H NMR (360 MHz, CDCl$_3$) δ2.31 (2H, d, J=3.0 Hz), 2.35 (1H, dt, J=12.0, 3.5 Hz), 2.80 (1H, d, J=12.9 Hz), 2.83 (1H, br d, J=11.0 Hz), 3.52 (1H, s), 3.59 (1H, dq, J=10.1, 1.6 Hz), 3.68 (1H, d, J=13.2 Hz), 3.88 (1H, d, J=16.6 Hz), 4.03 (1H, d, J=16.6 Hz), 4.18 (1H, dt, J=11.7, 2.5 Hz), 7.05 (1H, t, J=8.7 Hz), 7.19–7.32 (5H, m), 7.58 (2H, br s); MS (ES$^+$) 342 (M+1, 100%).

DESCRIPTION 14

(2R,3S)-(4-Aza-4-benzyl-1,7-dioxa-3-(4-fluorophenyl)spiro[5.4]dec-9-en-9-yl)trifluoromethanesulfonate The ketone of Description 13 (4.0 g, 11.7 mmol) as a solution in anhydrous tetrahydrofuran (16 ml) was added dropwise over 10 minutes to a solution of sodium bis(trimethylsilyl)amide (14.0 ml of 1.0M solution in tetrahydrofuran; 14.0 mmol) cooled to below −70° C. The reaction mixture was stirred at this temperature for 2 hours before the addition of 2-[N,N-bis(trifluoromethylsulphonyl)amino]-5-chloropyridine (6.44 g, 16.4 mmol) in several portions. The solution was stirred at below −70° C. for ½ hour before being allowed to warm to room temperature overnight. The reaction was quenched with a saturated ammonium chloride solution (60 ml) and extracted with ethyl acetate (3×30 ml). The combined organic extracts were dried (MgSO$_4$) and concentrated in vacuo to yield a crude oil (13.2 g) which was further purified by flash silica gel chromatography eluting with 10% ethyl acetate in hexane to yield the title compound as an orange oil (3.21 g, 58%) and recovered ketone (0.51 g, 13%). $^1$H NMR (360 MHz, CDCl$_3$) δ2.33 (1H, dt, J=12.0, 3.5 Hz), 2.83 (2H, d, J=13.5 Hz), 3.50 (1H, s), 3.68 (1H, m), 3.73 (1H, d, J=13.4 Hz), 3.94 (1H, dd, J=13.1, 2.1 Hz), 4.25 (1H, dt, J=11.7, 2.5 Hz), 4.57 (1H, dd, J-13.2, 2.1 Hz), 5.60 (1H, t, J=2.0 Hz), 7.01 (2H, t, J=8.7 Hz), 7.22–7.31 (5H, m), 7.48 (2H, br s);

MS (ES$^+$) 474 (M+1, 100%).

DESCRIPTION 15

(2-Methoxyphenyl)boronic acid n-Butyl lithium (13.0 ml of a 1.6M solution in hexanes, 19.8 mmol) was added dropwise to a solution of 2-bromoanisole (3.74 g, 19.0 mmol) in anhydrous tetrahydrofuran (15 ml) cooled to below −70° C., maintaining the temperature during the addition below −60° C. The solution was stirred for 20 minutes before the addition of trimethyl borate (5.9 ml, 57.0 mmol), and then stirred at below −70° C. for a further hour before warming to room temperature overnight. The reaction mixture was cooled to 0° C. acidified to pH 5.0 with 5% aqueous hydrochloric acid solution (25 ml), the resulting layers separated and the aqueous phase extracted with ethyl acetate (2×25 ml). The combined orgnic layers were washed with brine (25 ml), dried (MgSO$_4$) and concentrated in vacuo to yield the title compound as a white solid (2.9 g, 97%) which was used without further purification.

DESCRIPTION 16

(2-(3RS)-RS,3S)-4-Benzyl-2-[3-(tert-butyl-dimethyl-silanyloxy)-3-phenyl-prop-1ynyl]-3-(4-fluorophenyl)-morpholin-2-ol The title compound was prepared from the product of Description 6 (19.7 g, 79.9 mmol) and (3S)-4-benzyl-3-(4-fluorophenyl)-2-morpholinone (22.8 g, 80.0 mmol) according to the method of Description 7 as an orange oil (29.5 g, 69%). MS (ES$^+$) 532 (M+1, 100%), 514 (M—OH, 20).

DESCRIPTION 17

(2-(3RS)-RS,3S)-4-Benzyl-2-[3-(tert-butyl-dimethyl-silanyloxy)-3-phenyl-propyl]-3-(4-fluorophenyl)-morpholin-2-ol The title compound was prepared from the product of Description 16 (22.0 g, 41.3 mmol) according to the method of Description 8 as a crude oil (15.6 g, 70%). MS (ES$^+$) 536 (M+1, 100%), 518 (M—OH, 92).

DESCRIPTION 18

(2-(3RS)-RS,3S)-4-Benzyl-3-(4-fluorophenyl)-2-hydroxy-2-(3-hydroxy-3-phenyl-propyl)-morpholin-2-ol The title compound was prepared from the product of Description 17 (15.6 g, 29.1 mmol) according to the method of Description 9 as a viscous oil (5.3 g, 43%). MS (ES⁺) 422 (M+1, 55%), 404 (M—OH, 100).

DESCRIPTION 19

2-(2-Trifluoromethyl-phenyl)oxirane

α,α,α-trifluoro-o-tolualdehyde (3 g) was dissolved in anhydrous tetrahydrofuran and cooled to −78° C., iodochloromethane (1.38 ml) was then added, followed by methyllithium (1.5M complexed with lithium bromide) (12 ml) added over 5 minutes. The reaction was left to warm up to room temperature overnight. The reaction was quenched using saturated ammonium chloride solution and extracted using diethyl ether (2×50 ml). The combined organic extracts were washed with brine, dried (MgSO₄) and concentrated to afford a brown oil. Purification on flash silica eluted with 100% hexane up to 5% EtOAC in hexane afforded a colourless oil (1.1 g). ¹H NMR (250 MHz, CDCl₃) δ2.61–2.71 (1H, dd), 3.14–3.25 (1H, dd), 4.17–4.27 (1H, m), 7.33–7.70 (5H, m).

DESCRIPTION 20

2-(2-Trifluoromethyl-phenyl-4-trimethyl-silanyl-but-3-yn-1-ol

Using the chemistry described in *Chem Ber.* (1988), 121, 1315–1320, the oxirane of Description 19 was opened using the titanium complex chemistry to give the title compound. ¹H NMR (250 MHz,CDCl₃) δ0.19 (9H, s), 2.01–2.09 (1H, dd), 3.58–3.69 (1H, m), 3.78–3.88 (1H, m), 4.28–4.34 (1H, m), 7.34–7.41 (1H, t), 7.51–7.59 (1H, t), 7.60–7.66 (1H, d), 7.74–7.80 (1H, d).

The alcohol of Description 20 was taken through the series of steps described in Descriptions 1 to 5 to afford the corresponding diol intermediates:

DESCRIPTION 21

(a) 2-(2-Trifluoromethyl-phenyl)-but-3-yn-1-ol

¹H NMR (250 MHz, CDCl₃) δ2.34–2.45 (1H, m), 2.62 (1H, d), 3.94–4.22 (2H, m), 4.54–4.64 (1H, m), 7.62–7.94 (1H, t), 7.82–7.98 (2H, t+d), 8.04–8.13 (1H, d).

(b) tert-Butyldimethylsiloxy-2-(2-trifluoromethyl-phenyl)-but-3-yne

¹H NMR (250 MHz, CDCl₃) δ0.012 (6H, s), 0.86 (9H, s), 2.22 (1H, d, J=2.5 Hz), 3.77–3.91 (2H, m), 4.21–4.27 (1H, m), 7.32–7.42 (1H, t), 7.52–7.61 (1H, t), 7.62–7.68 (1H, d), 7.78–7.84 (1H, d).

(c) 4-Benzyl-2-[4-(tert-butyl-dimethyl-silanyloxy)-3-(2-trifluoromethyl-phenyl)-but-1-ynyl]-3(4-fluorophenyl)-morpholin-2ol

MS CI⁺ 614 (M+1⁺, 100%).

(d) 4-Benzyl-2-[4-(tert-butyl-dimethyl-silanyloxy)-3-(2-trifluoromethyl-phenyl)-butyl)-3-(4-fluorophenyl)-morpholin-2-ol Two products were observed from this hydrogenation. After isolation, by flash chromatography (eluant 10–20% ethyl acetate in hexane), the two pairs of isomers were carried thought the next two reactions individually.

Spot 1 higher R_f MS CI⁺ m/z 618 (M+1⁺, 100%)
Spot 2 lower R_f MS CI⁺ m/z 618 (M+1⁺, 100%).

(e) 4-Benzyl-2-(4-hydroxy-3-(2-trifluoromethyl-phenyl)-butyl)-3-(4-fluorophenyl)-morpholin-2-ol MS CI⁺ m/z 504 (M+1⁺, 100%).

DESCRIPTION 22

2-(3-Trifluoromethyl-phenyl) oxirane

Prepared according to the method of Description 19 starting from α,α,α-trifluoro-m-tolualdehyde. ¹H NMR (250 MHz, CDCl₃) δ2.75–2.83 (1H, m), 3.14–3.23 (1H, m), 3.89–3.96 (1H, m), 7.43–7.62 (4H, m).

DESCRIPTION 23

2-(3-Trifluoromethyl-phenyl)-4-trimethyl-silanyl-but-3-yn-1-ol

Using the chemistry described in *Chem. Ber.* (1988), 121, 1315–1320, the oxirane of Description 22 was opened using the titanium complex chemistry to give the title compound. ¹H NMR (250 MHz, CDCl₃) δ0.21 (9H, s), 1.88–1.95 (1H, t), 3.73–3.82 (2H, m), 3.92–3.99 (1H, m), 7.45–7.70 (4H, m).

The alcohol of Description 23 was taken through the series of steps described in Descriptions 1 to 5 to afford the corresponding diol intermediates:

DESCRIPTION 24

(a) 2-(3-Trifluoromethyl-phenyl)-but-3-yn-1-ol

¹H NMR (250 MHz, CDCl₃) δ1.95–2.04 (1H, m), 2.41 (1H, d, J=2.5 Hz) 3.78–3.87 (2H, m), 3.90–3.99 (1H, m), 7.44–7.70 (4H, m).

(b) tert-Butyldimethylsiloxy-2-(3-trifluoromethyl-phenyl)-but-3-yne

¹H NMR (250 MHz, CDCl₃) δ0.01 (6H, s), 0.89 (9H,s), 2.39 (1H, d, J=2.5 Hz), 3.73–3.81 (1H, m), 3.87–3.95 (1H, m), 3.97–4.04 (1H, m), 7.48–7.76 (4H, m).

c) 4-Benzyl-2-[4-(tert-butyl-dimethyl-silanyloxy)-3-(3-trifluoromethyl-phenyl-but-1-ynyl]-3-(4-fluorophenyl)-morpholin-2-ol MS CI⁺ m/z 614 (M+1⁺, 100%).

(d) 4-Benzyl-2-[4-(tert-butyl-dimethyl-silanyloxy)-3-(3-trifluoromethyl-phenyl)-butyl]-3-(4-fluorophenyl)-morpholin-2-ol No useful separation between isomers was seen at this stage. MS CI⁺ m/z 618 (M+1⁺, 100%).

(e) 4-Benzyl-2-(4-hydroxy-3-(3-trifluoromethyl-phenyl-butyl)-3-(4-fluorophenyl)-morpholin-2-ol MS CI⁺ m/z 504 (M+1⁺, 100%).

DESCRIPTION 25

2-(2-Trifluoromethoxy-phenyl)oxirane

Prepared according to the method of Description 19 starting from α,α,α-trifluoromethoxy-o-benzylaldehyde and purified by distillation B_{p7mm}60° C. ¹H NMR (250 MHz, CDCl₃) δ2.67–2.74 (1H, m), 3.16–3.24 (1H, m), 4.14–4.20 (1H, m), 7.20–7.38 (4H, m).

DESCRIPTION 26

2-(2-Trifluoromethyl-phenyl-4-trimethyl-silanyl-but-3-yn-1-ol

Using the chemistry described in *Chem. Ber.* (1988) 121, 1315–1320, the oxirane of Description 25 was opened using the titanium complex chemistry to give the title compound. $^1$H NMR (250 MHz, CDCl$_3$) δ0.21 (9H, s), 1.93–2.01 (1H, m), 3.58–3.86 (2H, m), 4.25–4.31 (1H, m), 7.23–7.38 (3H, m), 7.61–7.67 (1H, m).

The alcohol of Description 26 was taken through the series of steps described in Descriptions 1 to 5 to afford the corresponding diol intermediates:

DESCRIPTION 27

(a) 2-(2-Trifluoromethyl-phenyl)-but-3-yn-1-ol $^1$H NMR (250 MHz, CDCl$_3$) δ2.03–2.09 (1H, m), 2.45 (1H, d, J=2.5 Hz), 3.62–3.70 (2H, m), 4.26–4.30 (1H, m), 7.29–7.42 (3H, m), 7.60–7.68 (1H, m).

(b) tert-Butyldimethylsiloxy-2-(2-trifluoromethoxy-phenyl-but-3-yne $^1$H NMR (360 MHz, CDCl$_3$) δ0.01 (6H, s), 0.87 (9H, s), 2.24 (1H, d, J=2.5 Hz), 3.81–3.84 (2H, m), 4.20–4.25 (1H, m), 7.24–7.33 (3H, m), 7.66–7.70 (1H, m)

(c) 4-Benzyl-2-[4-(tert-butyl-dimethyl-silanyloxy)-3-(2-trifluoromethoxy-phenyl)-but-1-ynyl]-3-(4-fluorophenyl)-morpholin-2-ol MS CI$^+$ m/z 630 (M+1$^+$, 100%).

(d) 4-Benzyl-2-[4-tert-butyl-dimethyl-silanyloxy)-3-(2-trifluoromethoxy-phenyl)-butyl]-3-(4-fluorophenyl)morpholin-2-ol MS CI$^+$ m/z 634 (M+1$^+$, 100%).

(e) 4-Benzyl-2-(4-hydroxy-3-(2-trifluoromethoxy-phenyl-butyl-3-(4-fluorophenyl)-morpholin-2-ol MS CI$^+$ m/z 520 (M+1$^+$, 20%).

DESCRIPTION 28

4-Hydroxymethyl-N-(p-toluenesulfonyl)imidazole

4-Hydroxymethylimidazole hydrochloride (10 g) was suspended in dichloromethane (200 ml). p-Toluenesulfonyl chloride (15.58 g) was added and triethylamine (25.8 ml) was added dropwise to the stirred reaction mixture which was allowed to stir at room temperature overnight. The mixture was washed with water (2×100 ml) and brine (1×100 ml) and the organic layer was dried and evaporated to leave a clear oil which was recrystallised from ethyl acetate/hexane to afford the title compound as a white crystalline solid (15 g, 80%). $^1$H NMR (360 MHz, CDCl3) δ2.44 (3H, s), 4.55 (2H, s), 7.21 (1H, s), 7.35 (2H, d, J=8.0 Hz), 7.62 (2H, d, J=8.0 Hz 7.98 (1H, s). MS (CI$^+$) m/z 253 (M+H, 100%).

DESCRIPTION 29

((N-p-Toluenesulfonyl)imidazol-2-yl)methyl methanesulfonate

The product of Description 28 (1 g) was dissolved in dichloromethane (15 ml) and the solution was cooled in an ice-methanol bath. Triethylamine (0.4 g) was added dropwise in dichloromethane (1 ml) followed by methanesulfonyl chloride (0.45 g). The mixture was washed with water (2×10 ml) and brine (1×10 ml) and the organic layer was dried and evaporated to give the title compound as a white crystalline powder (1.3 g). $^1$H NMR (360 MHz, CDCl$_3$) δ2.45 (3H, s), 3.00 (3H, s), 5.13 (2H, s), 7.39 (2H, d, J=8.0 Hz), 7.40 (1H, s), 7.84 (2H, d, J=8.0 Hz), 8.00 (1H, s). MS (CI$^+$) m/z 267 ((M—CH$_3$O)$^+$, 30%).

EXAMPLE 1

(2S,3S,9R)-4-Aza-4-benzyl-1,7-dioxa-3,9-diphenyl-spiro[5.5]undecane (Isomer A)

The diol described in Description 5 (5 g) was suspended in hydrochloric acid (200 ml) and methanol was added to aid dissolution (50 ml). The resulting mixture was heated at reflux for 2 h. TLC (25% ethyl acetate in hexane) confirmed all starting material had reacted to give a mixture of 4 products. Hydrochloric acid was removed in vacuo and the residue was treated with sodium bicarbonate solution. The mixture was extracted with ethyl acetate (×3) and the combined organics were washed with brine, dried (MgSO$_4$) and evaporated to afford a yellow oil. This oil was purified on silica using 1–5% ethyl acetate in hexane as eluant. This removed Isomer A, the first component to elute, which was recrystallised from isopropanol to afford the title compound as white crystals. MS CI$^+$ m/z 400 (M+1$^+$, 100%).

EXAMPLE 2

2S,3S,9S)-4-Aza-4-benzyl-1,7-dioxa-3,9-diphenyl-spiro[5.5]undecane (Isomer B1)

The second fraction to elute from the column described in Example 1 comprised a 1:1 mixture of isomers, inseparable by chromatography. The mixture was separated by fractional crystallisation from isopropanol to afford the title compound as colourless needles. MS CI$^+$ m/z 400 (M+1$^+$, 100%).

EXAMPLE 3

2R,3S,9S)-4-Aza-4-benzyl-1,7-dioxa-3,9-diphenyl-spiro[5.5]undecane (Isomer B2)

The mother liquors from the crystallisation described in Example 2 were concentrated and recrystallised from isopropanol (×2) to afford the title compound as colourless prisms. MS CI$^+$ m/z 400 (M+1$^+$, 100%).

EXAMPLE 4

(2R,3S,9R)-4-Aza-4-benzyl-1,7-dioxa-3,9-diphenyl-spiro[5.5]undecane (Isomer C)

The third fraction to elute from the column described in Example 1 was concentrated to afford the title compound as a colourless oil. MS CI$^+$m/z 400 (M+1$^+$, 100%).

EXAMPLE 5

(2S,3S,9R)-4-Aza-1,7-dioxa-3,9-diphenylspiro[5.5]undecane

The product of Example 1 (Isomer A) (0.2 g) was dissolved in ethyl acetate with HCl (50 ml), wetted palladium on carbon (20%) (120 mg) was added and the reaction placed under an atmosphere of hydrogen, 40 psi. When TLC (20% ethyl acetate in petrol) showed no starting material the catalyst was removed in vacuo. The resultant yellow oil was purified on flash silica eluted with 20% ethyl acetate in petrol going up to 10% methanol in ethyl acetate to afford the title compound. MS CI$^+$ m/z 310 (M+1$^+$, 100%). $^1$H NMR (360 MHz, DMSO) HCl salt δ1.22–1.33 (1H, m), 1.59–1.68 (1H, m), 1.77–1.86 (1H, m), 1.90–2.04 (1H, m), 2.46–2.58 (1H, m) 3.16 (1H, s), 3.22–3.37 (2H, m), 3.60–3.68 (1H, t), 3.71–3.79 (1H, m), 3.87–396 (1H, m), 3.96–4.08 (1H, m), 4.5 (1H, s), 7.18–7.32 (5H, m), 7.41–7.51 (3H, m), 7.55–7.62 (2H, m).

EXAMPLE 6

(2S,3S,9S)4-Aza-1,7-dioxa-3,9-diphenyl-spiro[5,5] undecane

The product of Example 2 (Isomer B1) (0.44 g) was dissolved in methanolic ethyl acetate, wetted palladium on carbon (10%) (0.2 g) was added and the reaction put under an atmosphere of hydrogen 40 psi overnight. The catalyst was removed by filtration to afford the title compound as a white crystalline solid upon evaporation. MS CI$^+$ m/z 310 (M+1$^+$, 100%). $^1$H NMR (360 MHz, DMSO) δ1.07–1.19 (1H, m), 1.38–1.47 (2H, m), 2.18–2.31 (1H, m), 2.82 (1H, br s), 3.26–3.36 (2H, m), 3.89–4.10 (4H, m), 4.42 (1H, s), 6.91–7.05 (5H, m), 7.42–7.49 (3H, m), 7.52–7.60 (2H m).

EXAMPLE 7

(2S, 3S,9S)-4-Aza-1,7-dioxa-3,9-diphenyl-spiro[5.5] undecane-4-ylmethyl)-2,4-dihydro-1,2,4-triazol-3-one The compound of Example 6 (0.25 g) was suspended in N,N'-dimethylformamide (2.6 ml) with potassium carbonate (0.3 g) and N-methylcarboxy-2-chloroacetamidrazone (see EP-0577394-A) (0.134 g) and heated at 70° C. for one hour. The dark yellow mixture was heated to 140° C. to effect cyclisation. TLC in 5% methanol in ethyl acetate showed a good separation between the starting material, the acyclic and cyclic products. The mixture was diluted with water (30 ml) and ethyl acetate (10 ml). The organic layer was washed with water (2×30 ml), brine, dried (MgSO$_4$) and evaporated to afford a dark yellow semi-solid. Trituration with dichloromethane gave the title compound as a buff coloured crystalline solid (0.1 g). MS CI$^+$ m/z 407 (M+1$^+$, 100%). $^1$H NMR (360 MHz, DMSO) HCl salt δ1.22–1.34 (3H, m), 2.16–2.30 (1H, m), 2.33–2.44 (1H, m), 2.66–2.82 (3H, m), 3.25 (1H, s), 3.28–3.36 (1H, m), 3.60–3.67 (1H, m), 3.72–3.79 (1H, m), 3.87–4.00 (2H, m), 6.81–6.91 (4H, m), 6.94–7.00 (1H, m), 7.33 (3H, br s), 7.5 (1H, br s), 11.18–11.27 (2H, m).

EXAMPLE 8

4-Aza-4-benzyl-1,7-dioxa-3,8-diphenyl-spiro[5.4] decane

The diol described in Description 9 (0.16 g) was dissolved in anhydrous ether, boron trifluoride etherate was added dropwise, which formed a gummy solid on contact. Dichloromethane was added to aid dissolution, the reaction was left stirring overnight. The ether was removed in vacuo and the boron complex was destroyed by stirring overnight in methanolic hydrogen chloride. The methanol was removed in vacuo to afford the title compound as a brown oil. MS CI$^+$ m/z 386 (M+1$^+$, 100%).

EXAMPLE 9

(2S,3S,9S)-4-Aza-1,7-dioxa-3-(4-fluorophenyl)-9-phenylspiro[5.4]decane (a) (2R,3S)-4-Aza-4-benzyl-1,7-dioxa-3-(4-fluorophenyl)-9-phenylspiro[5.4]dec-9-ene The enol triflate of Description 14 (240 mg, 0.51 mmol) was dissolved in anhydrous 1,2-dimethoxyethane (1.75 ml) under an inert atmosphere. Sodium bicarbonate solution (0.76 ml of a 2.0M solution, 1.52 mmol) was added followed by phenylboronic acid (87 mg, 0.7 mmol), lithium chloride (64 mg, 1.52 mmol) and tetrakis(triphenylphosphine) palladium (0) (29 mg, 0.025 mmol) and the resulting mixture heated at reflux for 1½ hours. The reaction mixture was concentrated in vacuo and the residue partitioned between ethyl acetate (20 ml) and water (20 ml). The organic fraction was washed with water (2×20 ml) and brine (20 ml), dried (MgSO$_4$) and concentrated in vacuo to a brown gum which was further purified by flash silica gel chromatography eluting with 10% ethyl acetate in hexane to yield the title compound as a white solid (152 mg, 75%).

$^1$H NMR (360 MHz, CDCl$_3$) δ2.38 (1H, ddd, J=3.5, 12, 12), 2.83 (2H, m), 3.61 (1H, s), 3.73 (2H, m), 4.31 (2H, m), 4.97 (1H, dd, J=2, 13), 5.92 (1H, t, J=2), 6.92 (1H, t, J=8.8), 7.12 (2H, m), 7.25 (9H, m), 7.53 (2H, brm); MS (ES$^+$) m/z 402 (M+1, 100%).

(b) 2S,3S,9S)-4-Aza-1,7-dioxa-3-(4-fluorophenyl)-9-phenylspiro[5.4]decane

The alkene of step (a) (90 mg, 0.22 mmol) was hydrogenated overnight at 40 psi in methanol (15 ml) and chloroform (16 µl) over 10% palladium on charcoal (0.15 g). The catalyst was removed by filtration through a pad of Hyflo™, and the solvent evaporated. The residue was partitioned between dilute sodium bicarbonate (20 ml) and ethyl acetate (20 ml) and the combined organic extracts dried (MgSO$_4$) and concentrated in vacuo. Further purification by flash silica gel chromatography eluting with 50–100% ethyl acetate in hexane, afforded the title compound as a colourless oil (61 mg, 87%).

$^1$H NMR (500 MHz, CDCl$_3$) δ1.71 (1H, dd, J=10.2, 12.7), 2.22 (1H, m), 3.04 (1H, dd, J=2.2, 12.3), 3.19 (1H, m), 3.62 (3H, m), 4.10 (1H, s), 4.21 (1H, m), 4.34 (1H, t, J=8), 6.77 (2H, dd, J=1.8, 8.1), 7.03 (2H, t, J=8.7), 7.13 (3H, m), 7.49 (2H, dd, J=5.6, 8.7); MS (ES$^+$) m/z 314 (M+1, 100%).

EXAMPLE 10

2S,3S,9S)-4-Aza-1,7-dioxa-3-(4-fluorophenyl)-9-(2-methoxyphenyl) spiro[5.4]decane (a) (2S,3S)-4-Aza-4-benzyl-1,7-dioxa-3-(4-fluorophenyl)-9-(2-methoxyphenyl)spiro[5.4]dec-9-ene The rifle compound was obtained from the boronic acid of Description 15 (288 mg, 1.90 mmol) according to the method of Example 9, step (a), as a pale yellow foam (181 mg, 66%).

$^1$H NMR (250 MHz, CDCl3) δ2.38 (1H, ddd, J=3.5, 12,12), 2.82 (2H, m), 3.62 (1H, s), 3.78 (3H, s), 3.8–3.7 (2H, m), 4.32 (2H, m), 4.98 (1H, dd, J=2, 12.9), 6.15 (1H, t, J=2), 6.96–6.80 (5H, m), 7.13–7.18 (6H, m), 7.54 (2H, brs); MS (ES$^+$) m/z 432 (M+1, 100%).

(b) (2S,3S,9S)-4-Aza-1,7-dioxa-3-(4-fluorophenyl)-9-(2-methoxyphenyl) spiro[5.4]decane The alkene of step (a) (200 mg, 0.46 mmol) was dissolved in warm methanol (5 ml) and degassed with nitrogen for 5–10 minutes. Ammonium formate (500 mg) and 10% palladium on charcoal (100 mg) were added, the reaction flask purged with nitrogen, and the resulting suspension heated at reflux for 2–24 hours. The cooled reaction mixture was filtered through a pad of Hyflo™, and concentrated in vacuo to a crude gum which was purified by flash silica gel chromatography eluting with 67–100% ethyl acetate in hexane (or 4–8% methanol in dichloromethane) to yield the title compound as a colourless oil (80 mg, 51%).

¹H NMR (250 MHz, CDCl₃) δ1.80 (1H, m), 2.08 (1H, m), 3.03 (1H, dd, J=2, 12), 3.20 (1H, ddd, J=3.6, 12, 12), 3.65–3.55 (5H, m), 3.96 (1H, m), 4.01 (1H, s), 4.23 (1H, m), 4.33 (1H, t, J=8), 6.72–6.64 (3H, m), 7.26–6.97 (3H, m), 7.49 (2H, m); MS (ES⁺) m/z 344 (M+1, 100%).

EXAMPLE 11

(2S,3S,9S)-4-Aza-4-(2,3-dihydro-3-oxo-1,2,4-triazol-5-yl)methyl-1,7-dioxa-3-(4-fluorophenyl)-9-(2-methoxyphenyl)spiro[5.4]decane The title compound was obtained from the compound of Example 10 (70 mg, 0.2 mmol) according to the method of Example 7 as white needles (50 mg, 56%). Mp 237°–238° C. (toluene).

¹H NMR (250 MHz, CDCl₃) δ1.90 (1H, m), 2.12 (1H, m), 2.54 (1H, m), 2.89 (2H, m), 3.67–3.48 (7H, m), 3.89 (1H, m), 4.20 (1H, m), 4.35 (1H, t, J=8), 6.57 (1H, m), 6.73 (2H, m), 7.19–7.01 (3H, m), 7.59 (2H, brs), 9.9 (1H, s), 10.6 (1H, s); MS (ES⁺) m/z 441 (M+1, 100%).

EXAMPLE 12

(2R,3S,8R)-4-Aza-4-benzyl-1,7-dioxa-3-(4-fluorophenyl)8-phenyl-spiro[5.4]decane (Isomer A) and (2R,3S,8S)-4-Aza-4-benzyl-1,7-dioxa-3-(4-fluorophenyl)8-phenyl-spiro[5.4]decane (Isomer B)

The diol of Description 18 (2.4 g, 5.7 mmol) was heated at reflux in a solution of 6N hydrochloric acid (127 ml) and methanol (38 ml) for 18 hours. The methanol was evaporated in vacuo and the aqueous residue neutralised to pH 7–8 with sodium carbonate. The resulting solution was extracted with ethyl acetate (3×200 ml), the combined organic extracts dried (MgSO₄) and concentrated in vacuo to an orange oil (3.0 g). The crude concentrate was purified by flash silica gel chromatography eluting with 8–20% ethyl acetate in hexane to yield the separated title compounds as viscous oils which solidified on standing (1.05 g total, 46%).

Isomer A:-R_f 0.29 (10% ethyl acetate in hexane);

Analysis: C₂₆H₂₆FNO₂ requires C, 77.57: H, 6.50; N, 3.47; Found: C 77.16; H, 6.38; N, 3.37%):

¹H NMR (360 MHz, CDCl₃) δ1.77–2.00 (3H, m), 2.34 (1H dt, J=11.9, 3.5 Hz), 2.78 (2H, d, J=13.2 Hz), 3.49 (1H, s), 3.65 (1H, d, J=13.3 Hz), 3.64–3.69 (1H, m), 4.38 (1H, dt, J=11.7, 2.4 Hz), 4.46 (1H, dd, J=8.9, 5.6 Hz), 7.04 (2H, t, J=8.8 Hz), 7.17–7.35 (10H, m), 7.63 (2H, br s); MS (ES⁺) 404 (M+1, 100%).

Isomer B:-R_f 0.24 (10% ethyl acetate in hexane);

¹H NMR (250 MHz, CDCl₃) δ1.08–1.17 (1H, m), 1.90–2.21 (3H, m), 2.33 (1H, dt, J=11.9, 3.5 Hz), 3.11 (2H, d, J=13.8 Hz), 3.54 (1H, s), 3.55–3.60 (1H, m), 3.70 (1H, d, J=13.3 Hz), 4.23 (1H, dt, J=11.7, 2.5 Hz), 4.98 (1H, dd, J=8.4, 6.7 Hz), 7.01–7.08 (4H, m), 7.15–7.33 (8H, m), 7.65 (2H, br s); MS (ES⁺) 404 (M+1, 100%).

EXAMPLE 13

2R,3S,8R)-4-Aza-1,7-dioxa-3-(4-fluorophenyl)-8-phenyl-spiro[5.4]decane hydrochloride Isomer A of Example 12 (303 mg, 0.75 mmol) was dissolved in methanol (15 ml) and chloroform (2 μl, 0.25 mmol), and hydrogenated at 40 psi with 10% palladium on charcoal (200 mg) for 4 hours. The solution was filtered through a pad of Hyflo™, concentrated to dryness in vacuo and the residual solid (234 mg) recrystallised to give the title compound as a white solid (100 mg). m.p. 260–261° C. (dec.) (methanol-ethyl acetate).

Analysis: C₁₉H₂₀FNO₂.HCl.0.3H₂O requires C, 64.24; H, 6.13; N, 3.94; Found: C, 64.19; H, 5.95; N, 3.84%.

¹H NMR (360 MHz, d₆-DMSO) δ1.60–1.70 (1H, m), 1.78–1.94 (1H, m), 1.98–2.10 (2H, m), 3.25–3.32 (2H m), 3.96 (1H, br d, J=11.9 Hz), 4.30 (1H, m), 4.69–4.74 (1H, m), 4.74 (1H, s), 7.30–7.39 (7H, m), 7.70 (2H, dd, J=8.7, 5.5 Hz), 9.5–9.8 (~1H, vbr s), 9.9–10.3 (~1H, vbr s); MS (ES⁺) 314 (M+1, 100%).

EXAMPLE 14

2R,3S,9S)-4-Aza-1,7-dioxa-3-(4-fluorophenyl)-8-phenyl-spiro[5.4]decane hydrochloride The title compound was prepared from Isomer B of Example 12 (455 mg, 1.13 mmol) according to the method of Example 13 to give, after recrystallisation, a white solid (194 mg). m.p. 234–235° C. (dec.) (methanolethyl acetate).

Analysis: C₁₉H₂₀FNO₂.1.35HCl requires C, 62.94; H, 5.94; N, 3.86; Found: C, 62.96: H, 5.71: N, 3.93%.

¹H NMR (360 MHz, d₆-DMSO) δ1.00–1.11 (1H, m), 1.97 (2H, m), 2.24 (1H, sextet, J=6.3 Hz), 3.26–3.32 (2H, m), 3.89 (1H, d, J=11.7 Hz), 4.21 (1H, m), 4.75 (1H, s), 5.05 (1H, dd, J=8.7, 6.5 Hz), 7.20 (2H, d, J=7.9 Hz), 7.26–7.35 (5H, m), 7.71 (2H, dd, J=8.7, 5.4 Hz), 9.6–10.3 (~2H, vbr s); MS (ES⁺) 314 (M+1, 100%).

EXAMPLE 15

(2R,3S,8R)-4-Aza-4-(2,3-dihydro-3-oxo-1,2,4-triazol-5-yl)methyl-1,7-dioxa-3-(4-fluorophenyl)-8-phenyl-spiro[5.4]decane The title compound was prepared from the product of Example 13 (192 mg, 0.55 mmol) according to the method of Example 7 as a foam (80 mg, 35%).

Analysis: C₂₂H₂₃FN₄O₃H₂O requires C, 61.67; H, 5.88; N, 13.08; Found: C, 61.75; H, 5.74; N, 12.28%

¹H NMR (360 MHz, CDCl₃) δ1.65–1.76 (1H, m), 1.82–2.01 (3H, m), 2.56 (1H, br t, J=11.6 Hz), 2.79 (1H, d, J=11.2 Hz), 2.90 (1H, d, J=14.6 Hz), 3.38 (1H, d, J=14.6 Hz), 3.55 (1H, s), 3.73 (1H, br d, J=9.4 Hz), 4.38 (1H, br t, J=11.7 Hz), 4.52 (1H, dd, J=9.1, 6.3 Hz), 7.05 (2H, t, J=8.6 Hz), 7.25–7.34 (5H, m), 7.54 (2H, br s), 9.46 (1H, s), 9.92 (~1H, br s); MS (ES⁺) 411 (M+1, 100%).

EXAMPLE 16

(2R,3S,8S)-4-Aza-4-(2,3-dihydro-3-oxo-1,2,4-triazol-5-yl)methyl-1,7-dioxa-3-(4-fluorophenyl)-8-phenyl-spiro[5.4]decane The title compound was prepared from the product of Example 14 (284 mg, 0.8 mmol) according to the method of Example 7 as a foam (86 mg, 26%).

Analysis: C₂₂H₂₃FN₄O₃.0.5H₂O requires C, 63.00; H, 5.77; N, 13.86; Found: C, 63.05; H 5.53; N, 13.14%.

¹H NMR (360 MHz, CDCl₃) δ1.10–1.16 (1H, m), 1.90–1.97 (~2H, m), 2.09–2.17 (1H, sextet, J=6.4 Hz), 2.51 (1H, dt, J=11.9 Hz, 3.5 Hz), 2.77 (1H, d, J=11.2 Hz), 2.87 (1H, d, J=14.5 Hz), 3.42 (1H, d, J=14.5 Hz), 3.56 (1H, s), 3.63 (1H, br d, J=11.4 Hz), 4.21 (1H, br t, J=11.7 Hz), 5.00 (1H, t, J=7.5 Hz) 7.01–7.07 (5H, m), 7.21–7.26 (4H, m), 7.56 (2H, br s), 9.64 (1H, s), 10.23 (~1H, br s); MS (ES⁺) 411 (M+1, 100%).

EXAMPLE 17

4-Aza-4-benzyl-7-dioxa-5-phenyl-9-(2-trifluoromethyl-phenyl)-spiro[5.5undecane (4 isomers)

The 2 pairs of isomers carried through from Description 21, steps (d) and (e), were cyclised separately according to the method of Example 1, each giving 2 isomers. After separation on flash silica, eluant 1–5% ethyl acetate in hexane, the 4 isomers were isolated. The product of Description 21 (d) spot 1 (2.32 g) was cyclised to afford:

Spot 1 higher $R_f$ (0.25 g) (2R,3S,9R) MS CI⁺ m/z 485 (M+1⁺, 100%)

Spot 2 lower $R_f$ (1.1 g) (2S,3S,9R) MS CI⁺ m/z 485 (M+1⁺, 100%)

The product of Description 21 (d) spot 2 (1.91 g) was cyclised to afford:

Spot 1 higher $R_f$ (0.28 g) (2S,3S,9S) MS CI⁺ m/z 485 (M+1⁺, 100%)

Spot 2 lower $R_f$ (0.8 g) (2R, 3S, 9S) MS CI⁺ m/z 485 (M+1⁺, 100%)

The four isomers were debenzylated (to give Examples 18–21) using the procedure described in Example 5 with final purification of each isomer on flash silica, eluting with 1% methanol in dichloromethane:

EXAMPLE 18

(2S,3S,9S)-4-Aza-1,7-dioxa-3-(4-fluorophenyl)-9-(2-trifluoromethyl-phenyl)spiro[5.5]undecane The hydrochloride salt recrystallised from ethyl acetate. MS CI⁺ m/z 396 (M+1⁺, 100%); ¹H NMR (360 MHz, d₆-DMSO HCl salt) δ1.21–1.38 (2H, m) 1.48–1.58 (1H, m), 2.18–2.32 (1H, m), 3.12 (1H, br s), 3.24–3.36 (2H, m), 3.86–4.10 (3H, m), 4.12–4.19 (1H, m), 4.55 (1H, br s), 7.00–7.06 (1H, m), 7.10–7.16 (1H, m), 7.30–7.45 (3H, m), 7.58–7.62 (1H, m), 7.67–7.74 (2H, m)

EXAMPLE 19

(3R,3S,9S)-4-Aza-1,7-dioxa-3-(4-fluorophenyl)-9-(2-trifluoromethyl-phenyl)spiro[5.5]undecane The hydrochloride salt was recrystallised from ethyl acetate. MS CI⁺ m/z 396 (M+1⁺, 100%); ¹H NMR (360 MHz, d₆-DMSO HCl salt) δ1.32–1.44 (1H, m), 1.61–1.70 (2H, m), 2.01–2.09 (1H, m), 2.96–3.04 (1H, m), 3.08–3.30 (2H, m), 3.65–3.74 (1H, m), 3.75–3.86 (1H, m), 4.00–4.10 (2H, m), 4.58–4.63 (1H, m), 7.29–7.36 (2H, m), 7.41–7.52 1H, m), 7.54–7.84 (5H, m), 9.58 (1H, br s).

EXAMPLE 20

(2R,3S,9R)-4-Aza-1,7-dioxa-3-(4-fluorophenyl)-9-(2-(trifluoromethyl)-phenyl)spiro[5.5]undecane The hydrochloride salt was recrystallised from ethyl acetate/hexane. MS CI⁺ m/z 396 (M+1⁺, 100%); ¹H NMR (360 MHz, d₆-DMSO HCl salt) δ1.31–1.52 (2H, m), 1.58–1.68 (1H, m), 2.02–2.14 (1H, m), 3.01–3.08 (1H, m), 3.15–3.31 (2H, m), 3.94–4.06 (2H, m), 4.08–4.19 (2H, m), 4.90 (1H, s), 7.30–7.40 (2H, t), 7.41–7.48 (1H, m), 7.49–7.56 (1H, m), 7.65–7.71 (1H, m), 7.82–7.89 (3H, m), 9.79 (1H, br s).

EXAMPLE 21

(2S,3S,9R)-4-Aza-1,7-dioxa-3-(4-fluorophenyl)-9-(2-trifluoromethyl)-phenyl)spiro[5.5]undecane The hydrochloride salt was recrystallised from ethyl acetate and methanol. MS CI⁺ m/z 396 (M+1⁺, 100%); ¹H NMR (360 MHz, d₆-DMSO HCl salt) δ1.15–1.27 (1H, m), 1.55–1.65 (1H, m), 1.81–1.88 (1H, m), 1.98–2.13 (1H, m), 2.72–2.84 (1H, m), 3.26–3.32 (2H, m), 3.63–3.71 (1H, m), 3.77–3.86 (1H, m), 3.92–4.10 (2H, m), 4.58 (1H, s), 7.29–7.38 (2H, m), 7.42–7.48 (1H, m), 7.54–7.71 (5H, m), 9.95 (1H, br s).

EXAMPLE 22

2S,3S,9S)-4-Aza-4-(5-(dimethylaminomethyl)-1,2,3-triazol-4-yl)methyl-1,7-dioxa-3-(4 fluorophenyl-9-(2-trifluoromethyl-phenyl) spiro[5.5]undecane

(a) 2S,3S,9S)-4-Aza-4-(4-chlorobut-2-ynyl-1,7-dioxa-3-(4-fluorophenyl-phenyl)spiro[5.5]undecane 1,4-Dichloro-2-butyne (0.071 ml) and potassium carbonate (65 mg) were stirred with anhydrous N'N'-dimethylformamide (2 ml) under nitrogen atmosphere. The reaction was heated to 50° C., and the product of Example 18 (63 mg) was added dropwise as a solution in N'N'-dimethylformamide. After 3 hours, the reaction mixture was dispersed between water and ethyl acetate. The aqueous layer was extracted with ethyl acetate (2×). The combined organic layers were washed with brine, dried (MgSO₄) and the solvent evaporated to afford a yellow oil. Purification on flash silica, eluting with 10–20% ethyl acetate in hexane afforded the title compound as a colourless oil (60 mg).

(b) 2S, 3S,9S)-4-Aza-4-azidobut-2-ynyl)-1,7-dioxa-3-(4-fluorophenyl-2-trifluoromethyl-phenyl)spiro [5.5]undecane The chloroalkyne of step (a) above (60 mg) was dissolved in dimethyl sulphoxide (3 ml) and sodium azide (10 mg) was added and stirred at room temperature for 3 hours. The reaction mixture was dispersed between ammonium chloride/ethyl acetate (4:1). The organic layer was washed with water, brine, dried (MgSO₄) and evaporated in vacuo to afford the title compound (55 mg). MS CI⁺ 534 (M+1⁺, 100%); ¹H NMR (360 MHz, CDCl₃) δ1.26–1.56 (3H, m), 2.20 (6H, s), 2.28–2.40 (1H, m), 2.54 (1H, m), 2.89–2.96 (1H, d, J=11 Hz), 3.09–3.15 (1H, br s), 3.25 (1H, d, J=14 Hz), 3.30 (1H, s), 3.41–3.49 (2H, m), 3.64–3.76 (2H, m), 3.84–3.9 (1H, m), 4.01–4.09 (1H, m), 4.14–4.20 (1H, m), 6.91–6.96 (1H, m), 7.40–7.19 (5H, m), 7.26 (1H, s), 7.49–7.53 (1H, m).

c) (2S,3S,9S)-4-Aza-4-(5-(dimethylaminomethyl)-1,2,3-triazol-4-yl)methyl-1,7-dioxa-3-(4-fluorophenyl)-9-(2-trifluoromethyl-phenyl)spiro[5.5]undecane The azide of step (b) (60 mg) was dissolved in dioxane (2 ml) and cooled to 0° C. under a blanket of nitrogen in a sealed tube. Dimethylamine (2 ml) was condensed into the solution and the tube was sealed tightly. The sealed tube was heated at 60° C. for 6 hours. By TLC (5% methanol in dichloromethane) no starting material remained. The solvent was removed in vacuo to afford a brown oil. This was purified by flash chromatography eluting with 5% methanol; 0.2% ammonia in dichloromethane to give the title compound. ¹H NMR (360 MHz, CDCl₃) δ1.26–1.56 (3H, m), 2.20 (6H, s), 2.28–2.40 (1H, m), 2.54 (1H, m), 2.89–2.96

(1H, d, J=11), 3.09–3.15 (1H, bs), 3.25 (1H, d, J=14), 3.30 (1H, s), 3.41–3.49 (2H, m), 3.64–3.76 (2H, m), 3.84–3.90 (1H, m), 4.01–4.09 (1H, m), 4.14–4.20 (1H, m), 6.91–6.96 (1H, m), 7.04–7.19 (5H, m), 7.26 (1H, s), 7.49–7.53 (1H, m). MS CI$^+$ m/z 534 (M+1, 100%).

EXAMPLE 23

4-Aza-4-benzyl-1,7-dioxa-3-(4-fluorophenyl)-9-(3-trifluoromethyl-phenyl)-spiro[5.5]undecane (4 isomers)

The product of Description 24(e) was cyclised according to the method of Example 1 to give four isomers were isolated by flash chromatography, eluant 1–10% ethyl acetate in hexane. This efficiently separated spot 1 (highest $R_f$) and spot 4 (lowest $R_f$). Spots 2 and 3 were isolated by lobar chromatography (eluant 1–5% ethyl acetate in hexane) and crystallisation from isopropyl alcohol.

Spot 1 (2S,3S,9R). MS CI$^+$ m/z 486 (M+1$^+$, 100%); $^1$H NMR (360 MHz, d$_6$-DMSO, salt) δ1.16–1.28 (1H, m), 1.62–1.71 (1H, m), 1.73–1.85 (1H, m), 1.84–2.03 (1H, m), 2.62–2.72 (1H, m), 3.16–3.54 (3H, m), 3.64–4.10 (5H, m), 4.62–4.72 (1H, m), 7.30–7.61 (13H, m).

Spot 2 (2R,3S,9S). MS CI$^+$ m/z 486 (M+1$^+$, 100%); $^1$H NMR (500 MHz, CDCl$_3$, free base) δ1.20–1.32 (1H, m), 1.64–1.72 (1H, m), 1.77–1.83 (1H, m), 1.99–2.08 (1H, m), 2.38–2.47 (1H, m), 2.77–2.91 (2H, m), 3.21 (1H, d, J=1 Hz), 3.38 (1H, d, J=14 Hz), 3.66 (1H, s), 3.76–3.86 (3H, m), 4.08–4.13 (1H, m), 7.01–7.09 (1H, m), 7.20–7.51 (12H, m).

Spot 3 (2R,3S,9R). MS CI$^+$ m/z 486 (M+1$^+$, 100%); $^1$H NMR (360 MHz, CDCl$_3$, free base) δ1.10–1.58 (4H, m), 2.28–2.46 (2H, m), 2.74–2.86 (3H, m), 3.16 (1H, s), 3.57–3.73 (2H, m), 3.96–4.14 (2H, m). 6.94–7.34 (13H, m).

Spot 4 (2S,3S,9S). MS CI$^+$ m/z 486 (M+1$^+$, 100%); $^1$H NMR (360 MHz, CDCl$_3$, free base) δ1.12–1.26 (1H, m), 1.46–1.69 (2H, m), 2.20–2.32 (1H, m), 2.37–2.47 (1H, m), 2.81–2.92 (2H, m), 3.03 (1H, d, J=14 Hz), 3.56 (1H, s), 3.62 (1H, d, J=14 Hz), 3.78–3.87 (1H, m), 3.99–4.10 (2H, m), 4.27–4.35 (1H, m), 6.95–7.02 (2H, m), 7.17–7.42 (10H, m), 7.52 (1H, s).

The four isomers were debenzylated (to give Examples 24–27) using the procedure described in Example 5 with final purification of each isomer on flash silica eluting with 1% methanol in dichloromethane:

EXAMPLE 24

2R,3S,9S)-4-Aza-1,7-dioxa-3-(4-fluorophenyl-9-3-trifluoromethyl-phenyl)spiro[5.5]undecane The hydrochloride salt was recrystallised from ethyl acetate and methanol. MS CI$^+$ m/z 396 (M+1$^+$, 100%); $^1$H NMR (360 MHz, d$_6$-DMSO HCl salt) δ1.28–1.39 (1H, m), 1.67–1.79 (2H, m), 1.06–2.01 (1H, m), 2.94–3.05 (2H, m), 3.21–3.32 (1H, m), 3.61 (1H, N—H), 3.70–3.79 (1H, t), 3.81–3.87 (1H, m), 4.00–4.12 (2H, m), 4.54 (1H, s), 7.30–7.38 (2H, t), 7.55–7.64 (4H, m), 7.78–7.85 (2H, m).

EXAMPLE 25

(2R,3S,9R)-4-Aza-1,7-dioxa-3-(4-fluorophenyl)-9-(3-trifluoromethylphenyl)spiro[5.5]undecane MS CI$^+$ m/z 396 (M+1$^+$, 100%); $^1$H NMR (360 MHz, d$_6$-DMSO HCl salt) δ1.15–1.28 (1H, m), 132–1.41 (1H, m), 1.49–1.62 (1H, m), 2.33–2.45 (1H, m), 2.85 (1H, s), 3.11–3.31 (2H, m), 3.74–3.84 (1H, m), 3.94 (1H, s), 4.06–4.14 (1H, m), 4.16–4.35 (2H, m), 6.94–7.09 (3H, m), 7.13–7.21 (1H, m), 7.22–7.35 (2H, m), 7.30–7.63 (2H, m).

EXAMPLE 26

(2S,3S9R)-4-Aza-1,7-dioxa-3-(4-fluorophenyl)-9-(3-trifluoromethylphenyl)spiro[5.5]undecane MS CI$^+$ m/z 396 (M+1$^+$, 100%); $^1$H NMR (360 MHz, d$_6$-DMSO HCl salt) δ1.22–1.33 (1H, m), 1.64–1.73 (1H, m), 1.78–1.86 (1H, m), 1.90–2.04 (1H, m), 2.65–2.76 (1H, m), 3.24–3.36 (2H, m), 3.65–3.73 (1H, t), 3.78–3.84 (1H, m), 3.88–3.95 (1H, m), 3.97–4.07 (1H, m), 4.56 (1H, s) 7.28–7.37 (2H, t), 7.50–7.60 (4H, m), 7.62–7.69 (2H, m).

EXAMPLE 27

2S,3S,9S)-4-Aza-1,7-dioxa-3-4-fluorophenyl)-9-(3-trifluoromethyl-phenyl)spiro[5.5]undecane MS CI$^+$ m/z 396 (M+1$^+$, 100%); $^1$H NMR (360 MHz, d$_6$-DMSO HCl salt) δ1.04–1.15 (1H, m), 1.61–1.72 (2H, m), 2.11–2.22 (1H, m), 3.00–3.12 (2H, m), 3.18–3.22 (1H, m), 4.00–4.18 (4H, m), 4.57 (1H, s), 7.24–7.33 (2H, m), 7.44–7.52 (1H, m), 7.53–7.58 (1H, m), 7.59–7.66 (2H, m), 7.72–7.80 (2H, m), 9.74 (1H, br s), 9.91 (1H, br s).

EXAMPLE 28

2S,3S,9S)-4-Aza-4-(5-(dimethylaminomethyl-1,2,3-triazol-4-yl)methyl-1,7-dioxa-3-(4-fluorophenyl)-9-(3-trifluoromethyl-phenyl)spiro[5.5]undecane Using the same chemistry as described in Example 22, the product of Example 27 (0.21 g) was taken through to the title compound (58 mg). MS CI$^+$ m/z 534 (M+1$^+$, 100%); $^1$H NMR (360 MHz, d$_6$-DMSO HCl salt) δ1.08–1.19 (1H, m), 1.45–1.61 (2H, m), 2.21–2.36 (7H, m+(CH$_3$)$_2$), 2.42–2.49 (1H, m), 2.84–3.94 (2H, m), 3.47 (2H, dd, J$_1$=14 Hz, J=14 Hz), 3.81 (2H, m), 4.05–4.12 (2H, m), 4.21–4.28 (1H, m), 6.97–7.04 (2H, t), 7.26–7.32 (1H, m), 7.37–7.48 (4H, m), 7.60 (1H, m),

EXAMPLE 29

(2S,3S,9S)-4-Aza-4-benzyl-7-dioxa-5-phenyl-9-(2-trifluoromethoxy-phenyl)-spiro[5.5]undecane Only one of the four possible isomers from the product of Description 27(e) was isolated by flash chromatography eluting with 1–5% ethyl acetate in hexane. The diol (4 g) was cyclised according to the method of Example 1 to give:

spot 1 highest $R_f$ (0.35 g) (2S,3S,9S) MS CI$^+$ m/z 502 (M+1$^+$, 100%); $^1$H NMR (360 MHz, CDCl$_3$, free base) δ1.22–1.60 (3H, m), 2.25–2.38 (2H, m), 2.78–2.88 (2H, m), 3.01–3.06 (1H, m), 3.19 (1H, s), 3.58–3.65 (1H, m), 3.71–3.76 (1H, d, J=13 Hz), 3.84–3.91 (1H, m), 3.99–4.15 (2H, m), 6.67–6.73 (1H, m), 6.91–6.96 (1H, m), 7.02–7.12 (3H, m), 7.20–7.33 (8H, m).

The rest of the isomers (2.9 g) were taken on to be debenzylated as a mixture.

EXAMPLE 30

2S,3S,9S)-4-Aza-1,7-dioxa-3-(4-fluorophenyl)-9-trifluoromethoxyphenyl)spiro[5.5]undecane The title compound of Example 29 was debenzylated according to the method of Example 5. The hydrochloride salt recrystallised from ethyl acetate. MS CI$^+$ m/z 412

(M+1⁺, 100%); ¹H NMR (360 MHz, d₆-DMSO HCl salt) δ0.81–0.89 (1H, m), 1.00–1.10 (1H, m), 1.21–1.26 (1H, m), 1.36–1.55 (2H, m), 2.19–2.32 (1H, m), 3.04–3.11 (1H, m), 3.33 (6H, s), 3.90–4.15 (4H, m), 4.51 (1H, s). 6.80–6.86 (1H, m), 7.03–7.05 (1H, m), 7.18–7.28 (2H, m), 7.35–7.41 (2H, m), 7.63–7.71 (2H, m).

EXAMPLE 31

4-Aza-1,7-dioxa-3-(4-fluorophenyl-9-(trifluoromethoxyphenyl)spiro[5.5]undecane

The mixture of isomers referred to in Example 29 after debenzylation showed 2 major isomers which were separated by Lobar chromatography with eluant 0.2% ammonia 0–2% methanol in dichloromethane. Two single isomers with stereochemistry undetermined in the 2 and 9 positions were obtained:

(a) Higher $R_f$. The free base recrystallised from diethyl ether/hexane. MS CI⁺ m/z 411 (M+1⁺, 100%); ¹H NMR (360 MHz, CDCl₃) δ1.22–1.33 (1H, m), 1.58–1.68 (1H, m), 1.84–2.09 (3H, m), 3.71–3.79 (1H, m), 3.10–3.21 (2H, m), 3.69–3.85 (4H, m), 3.96–4.04 (1H, m), 7.00–7.07 (2H, t), 7.19–7.36 (4H, m), 7.51–7.59 (2H, m).

(b) Lower $R_f$. The hydrochloride salt recrystallised from ethyl acetate and methanol. MS CI⁺ m/z 411 (M+1⁺, 100%); ¹H NMR (360 MHz, CDCl₃ HCl salt) δ1.36–1.47 (1H, m), 1.59–1.68 (1H, m), 1.73–1.81 (1H, m), 2.01–2.16 (1H, m), 2.90–3.01 (1H, m), 3.28–3.44 (2H, m), 3.64–3.72 (1H, t), 3.80–3.89 (2H, m), 4.11–4.17 (1H, s), 4.21–4.32 (1H, m), 7.09–7.17 (2H, t), 7.18–7.34 (4H, m), 7.69–7.75 (2H, m).

EXAMPLE 32

(2S,3S,9S)-4-Aza-4-(5-(dimethylaminomethyl)-1,2,3-triazol-4-yl)methyl-1,7-dioxa-3-(4-fluorophenyl)-9-(2-trifluoromethoxyphenyl)spiro[5.5]undecane Using the same chemistry as described in Example 22 the product of Example 30 (0.21 g) was reacted to give the the title compound (90 mg). MS CI⁺ m/z 550 (M+1⁺, 100%); ¹H NMR (360 MHz, CDCl₃) δ1.18–1.34 (3H, m), 1.41–1.49 (1H, m), 2.15–2.20 (6H, s), 2.24–2.38 (1H, m), 2.52–2.62 (1H, m), 2.88–2.94 (1H, m), 3.01–3.07 (1H, m), 3.20–3.26 (2H, m), 3.37–3.47 (2H, m), 3.63–3.74 (2H, m), 3.83–3.92 (1H, m), 4.01–4.16 (2H, m), 6.68–6.75 (1H, m), 6.96–7.12 (7H, m).

The following Examples (Table 1) were prepared according to the method of Example 9 from (2R,3S)-(4-aza-4-benzyl-yl-1,7-dioxa-3-(4-fluorophenyl)spiro[5.4]dec-9-en-9-yl) trifluoromethanesulfonate (Description 14) and the appropriate phenylboronic acid.

The following Examples (Table 2) were prepared according to the method of Example 22 from the corresponding Example from Table 1.

TABLE 1

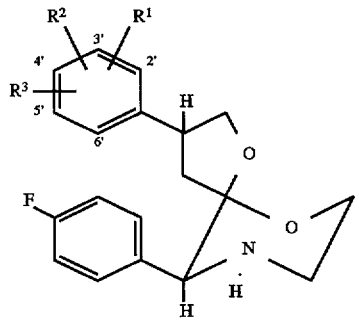

| Ex. No. | R¹ | R² | R³ | Data |
|---|---|---|---|---|
| 33 | 3'-CF₃ | H | H | ¹H NMR (250MHz, CDCl₃)δ 1.71(1H, m), 2.30(1H, m), 3.05–3.26(2H, m), 3.63(3H, m), 4.05(1H, s), 4.19–4.39(2H, m), 6.89(1H, m), 7.03(3H, m), 7.20 (1H, m), 7.38(1H, m), 7.48–7.54(2H, m); MS(ES⁺)m/z 381(M+1, 100%). |
| 34 | 2'-CF₃ | H | H | ¹H NMR(250MHz, CDCl₃)δ 1.64–1.91(2H, m), 2.24–2.36(1H, dd), 3.01–3.12 (1H, dt), 3.15–3.28(1H, td), 3.62–3.76(2H, m), 3.89–4.05(2H, m), 4.10–4.25 (1H, td), 4.29–4.38(1H, t), 6.27–6.46(1H, m), 6.96–7.20(4H, m), 7.42–7.58 (3H, m); MS(ES⁺)m/z 382(M+1, 100%). |
| 35 | 4'-OCH₃ | H | H | ¹H NMR(360MHz, CDCl₃)δ 1.66(1H, dd, J=12.7, 10.2), 1.87(1H, bs), 2.16 (1H, dd, J=12.7, 7.5), 3.03(1H, dd, J=12.3, 2.4), 3.18(1H, dt, J=12.2, 3.6), 3.45–3.75(3H, m), 3.72(3H, s), 4.00(1H, s), 4.21(1H, dt, J=11.8, 2.9), 4.31 (1H, t, J=7.9), 6.69(4H, s), 7.03(2H, t, J=8.7), 7.48(2H, m); MS(ES⁺)m/z 344(M+1, 100%), 326(M-17, 25). |
| 36 | 2'-CH₃ | H | H | ¹H NMR(250MHz, CDCl₃)δ 1.64(1H, dd, J=12.8, 10.1), 1.97–2.21(2H, m), 2.17(3H, s), 2.96(1H, dd, J=12.2, 2.2), 3.12(1H, dt, J=12.2, 3.6), 3.49(1H, t, J=8.0), 3.60(1H, dd, J=10.3, 2.4), 3.70–3.87(1H, m), 3.94(1H, s), 4.14(1H, dt, J=11.5, 3.0), 4.25(1H, t, J=8.2), 6.38(1H, m), 6.84–7.01(4H, m), 7.24(1H, m), 7.38–7.46(2H, m); MS(ES⁺)m/z 328(M+1, 100%), 310(M-17, 32). |
| 37 | 2'-OCF₃ | H | H | ¹H NMR(250MHz, CDCl₃)δ 1.74(1H, m), 2.25(1H, m) 3.07(1H, m) 3.25 (1H, m), 3.55–3.70(2H, m), 3.83–3.94(2H, m), 4.03(1H, m), 4.34(1H, m), 6.36 (1H, d, J=8.5Hz), 6.91–7.12(5H, m), 7.47–7.52(2H, m); MS(ES⁺)m/z 397 (M+1, 100%). |
| 38 | 3'-OCH₃ | H | H | ¹H NMR(360MHz, CDCl₃)δ 1.71(1H, dd, J=12.8, 10.0), 2.20(1H, dd, J=12.9, 7.5), 3.03(1H, dd, J=12.3, 2.1), 3.18(1H, dt, J=12.3, 3.6), 3.53–3.66(3H, m), 3.67(3H, s), 4.00(1H, s), 4.21(1H, dt, J=11.8, 3.0), 4.33(1H, t, J=7.4), 6.32 |

TABLE 1-continued

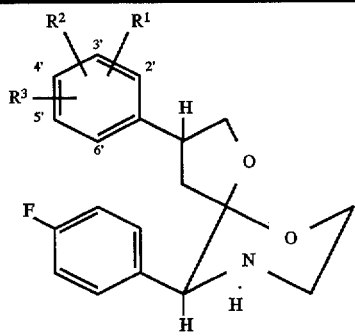

| Ex. No. | $R^1$ | $R^2$ | $R^3$ | Data |
|---|---|---|---|---|
| | | | | (1H, t, J=2.0), 6.39(1H, d, J=7.7), 6.65(1H, dd, J=8.3, 2.5), 6.99–7.08(3H, m), 7.47–7.52(2H, m); MS(ES$^+$)m/z 344(M+1, 100%). |
| 39 | 3'-NH$_2$ | H | H | $^1$H NMR(250MHz, CDCl$_3$)δ 1.74(1H, m), 2.22(1H, m), 3.06(1H, m), 3.33 (1H, m), 3.50–3.68(4H, m), 4.00(1H, s), 4.08–4.35(2H, m), 6.00(1H, m), 6.21 (1H, d, J=7.61Hz), 6.45(1H, m), 6.87–7.07(3H, m), 7.49(2H, m); MS(ES$^+$) m/z 328(M+1, 100%). |
| 40 | 3'-OCH(CH$_3$)$_2$ | H | H | $^1$H NMR(250MHz, CDCl$_3$)δ 1.26(6H, d, J=3.0), 1.65–1.75(1H, m), 2.20(1H, m), 3.01–3.25(2H, m), 3.52–3.68(3H, m), 4.00(1H, s), 4.16–4.52(3H, m), 6.29 (1H, m), 6.37(1H, d, J=7.7Hz), 6.65(1H, m), 6.99–7.07(3H, m), 7.50(2H, m). |
| 41 | 2'-OCH$_3$ | 5'-F | H | $^1$H NMR(250MHz, CDCl$_3$)δ 1.76(1H, dd, J=10, 12.5), 3.00–3.06(1H, m), 3.19 (1H, td, J=3.5, 12), 3.56(1H, t, J=7.7), 3.62(3H, s), 3.60–3.68(1H, m), 3.85–3.94(1H, m), 4.00(1H, s), 4.21(1H, td, J=3.5, 12), 4.31(1H, t, J=7.7), 6.29 (1H, dd, J=3, 9.5), 6.63(1H, dd, J=4.5, 9), 6.76(1H, td, J=3, 9.5), 7.00(2H, t, J=8.7)7.42–7.49(2H, m); MS(ES$^+$)m/z 362(M+1, 100%). |
| 42 | 2'-OCH$_3$ | 5'-OCH$_3$ | H | $^1$H NMR(360MHz, CDCl$_3$)δ 1.80(1H, dd, J=11, 12), 2.08(1H, dd, J=7.7, 12), 3.03(1H, dd, J=2, 12), 3.18(1H, dt, J=3.6, 12), 2.57(1H, t, J=8), 3.59(3H, s), 3.62(3H, s), 3.6(1H, dd, J=2, 12), 3.91(1H, m), 4.11(1H, s), 4.22(1H, dt, J=3.6, 12), 4.32(1H, t, J=8), 6.23(1H, dd, J=3), 6.61(1H, dd, J=3, 8.5), 6.66 (1H, d, J=8.5), 6.99(2H, t, J=8.6), 7.48(2H, dd, J=5.5, 8.6); MS(ES$^+$)m/z 374 (M+1, 100%). |
| 43 | 2'-OCH(CH$_3$)$_2$ | H | H | $^1$H NMR(250MHz, CDCl$_3$)δ 1.14–1.30(6H, m), 1.76(1H, dd, J=10.6 and 12.5Hz), 2.11(1H, dd, J=7.7 and 12.5), 2.21(1H, brs), 3.04(1H, dd, J=1.9 and 12.3), 3.19(1H, ddd, J=3.6, 12.2 and 12.2), 3.54(1H, dd, J=8 and 8), 3.67(1H, dd, J=2.3 and 11.3), 3.93–4.04(2H, m), 4.23(1H, ddd, J=3.1, 11.8 and 11.8), 4.34–4.52(2H, m), 6.56(1H, dd, J=1.7 and 7.6), 6.69(1H, dd, J=1.1 and 8.8), 6.74(1H, d, J=7.8), 6.95–7.14(3H, m), 7.44–7.53(2H, m); MS(ES$^+$)m/z 372 (M+1, 100%). |
| 44 | 2'-O(CH$_2$)$_2$CH$_3$ | H | H | $^1$H NMR(360MHz, d$_6$-DMSO)δ 0.92(3H, t, J=7.5), 1.57(2H, q, J=7.5), 1.73 (1H, t, J=10.8), 2.20(1H, dd, J=7.5, 12.6), 3.2–3.3(1H, m), 3.58(1H, t, J=8.5), 3.76–3.90(5H, m), 4.16–4.18(1H, m), 4.32(1H, t, J=8), 4.73(1H, s), 6.58(1H, d, J=6), 6.70(1H, t, J=6.8), 6.86(1H, d, J=7.5), 7.11(1H, t, J=8), 7.30(2H, t, J=9), 7.68(2H, dd, J=5, 8); MS(ES$^+$)m/z 372(M+1, 100%). |
| 45 | 2'-OCH(CH$_3$)$_2$ | 5'-F | H | $^1$H NMR(250MHz, d$_6$-DMSO)δ 1.13(6H, dd, J=6.1 and 6.1), 1.61–1.70(1H, m), 2.26(1H, dd, J=7.8 and 13.0), 3.20–3.40(3H, m), 3.64(1H, dd, J=7.9 and 7.9), 3.68–3.82(1H, m), 3.84–3.94(1H, m), 4.08–4.20(1H, m), 4.28(1H, dd, J=8.0 and 8.0), 4.42–4.54(1H, m), 4.77(1H, brs), 6.21(1H, d, J=9.7), 6.89 (2H, d, J=5.0), 7.30(2H, dd, J=8.8 and 8.8), 7.66(2H, dd, J=5.5 and 8.7); MS (ES$^+$)m/z 371(M+1, 100%). |
| 46 | 2'-OCH(CH$_3$)$_2$ | 5'-CH(CH$_3$)$_2$ | H | $^1$H NMR(250MHz, DMSO salt)δ 0.98–1.05(3H, d, J=7), 1.09–1.17(3H, m), 1.63–1.75(1H, m), 2.14–2.26(1H, m), 2.52–2.65(1H, m), 3.24–3.40(2H, m+H$_2$O), 3.50–3.58(1H, m), 3.77–3.95(2H, m), 4.12–4.34(2H, m), 4.36–4.52 (1H, m), 4.75(1H, s), 6.27–6.32(1H, m), 6.77–6.68(1H, m), 6.92–6.98(1H, m), 7.30–7.40(2H, m), 7.68–7.77(2H, m); MS(ES$^+$)m/z 414(M+1, 100%). |
| 47 | 2'-OCH$_3$ | 5'-CH(CH$_3$)$_2$ | H | $^1$H NMR(360MHz, DMSO)δ 1.02(6H, d, J=6.9), 1.75(1H, t, J=10.9), 2.15 (1H, m), 2.62(1H, m), 3.27(2H, m), 3.55(3H, s), 3.57(1H, t, J=8.2), 3.80(1H, m), 3.87(1H, m), 4.19(1H, m), 4.28(1H, t, J=8.3), 4.74(1H, s), 6.40(1H, d, J=2.2), 6.77(1H, d, J=8.5), 6.97(1H, dd, J=8.4, 2.2), 7.34(2H, t, J=8.9), 7.71 (2H, m); MS(ES$^+$)m/z 386(M+1, 100%). |
| 48 | 2'-OCH$_2$CH$_3$ | 5'-F | H | $^1$H NMR(360MHz, DMSO)δ 1.18(3H, t, J=7), 1.71(1H, m), 2.25(1H, m), 3.27(2H, m), 3.64(1H, t, J=7.8), 3.80(1H, t, J=8.3), 3.89(3H, m), 4.18(1H, m), 4.29(1H, t, J=8.2), 4.74(1H, s), 6.27(1H, dd, J=9.8, 3), 6.89(2H, m), 7.28 (2H, t, J=8.9), 7.67(2H, m); MS(ES$^+$)m/z 376(M+1, 100%). |
| 49 | 2'-OCH$_3$ | 5'-C(CH$_3$)$_3$ | H | $^1$H NMR(250MHz, CDCl$_3$)δ 1.16(9H, s), 1.88(1H, m), 2.11(1H, m), 3.07 (1H, m), 3.20(1H, m), 3.57(3H, s), 3.68(1H, m), 3.88(1H, m), 4.03(1H, s), 4.20–4.34(2H, m), 6.65(1H, d, J=8.5), 6.76(1H, d, J=2.5), 6.99–7.13(3H, m), 7.52(2H, m); MS(ES$^+$)m/z 399(M+1, 100%). |
| 50 | 2'-OH | H | H | $^1$H NMR(360MHz, CDCl$_3$)δ 1.82(1H, t, J=10.9), 2.10(1H, m), 3.06(1H, dd, J=12.4, 2.1), 3.19(1H, dt, J=12, 3.6), 3.56(1H, t, J=8.3), 3.65(1H, dd, J=11, 2.8), 3.96(1H, m), 4.03(1H, s), 4.23(1H, dt, J=11.8, 2.9), 4.37(1H, t, J=8.2). 6.54(2H, m), 6.72(1H, dd, J=8, 1.0), 6.96(3H, m), 7.50(2H, m); MS(ES$^+$) m/z 330(M+1, 100%). |

TABLE 1-continued

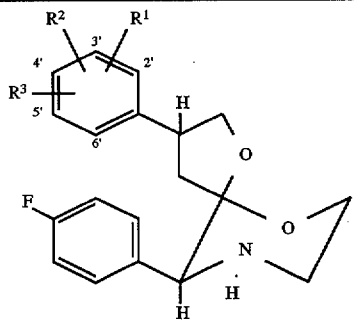

| Ex. No. | R[1] | R[2] | R[3] | Data |
|---|---|---|---|---|
| 51 | 2'-OCH$_2$CH$_2$-3' | | H | $^1$H NMR(360MHz, CDCl$_3$)δ 1.88(1H, dd, J=11, 12), 2.07(1H, dd, J=7.5, 12), 3.02(1H, dd, J=2, 12), 3.09(2H, t, J=8.5), 3.18(1H, td, J=3.6, 12), 3.62(1H, t, J=8.5), 3.62–3.73(2H, m), 3.99(1H, s), 4.22(1H, td, J=3.6, 12), 4.24–4.39(3H, m), 6.50(1H, d, J=7.7), 6.62(1H, t, J=7.5), 6.9–7.0(3H, m), 7.4–7.5(2H, m); MS(ES$^+$)m/z 356(M+1, 100%). |
| 52 | 2'-OCH$_3$ | 6'-F | H | $^1$H NMR(250MHz, CDCl$_3$)δ 1.87(1H, m), 2.19(1H, m), 3.05(1H, m), 3.20 (1H, dt, J=3.5, 12.1), 3.43(3H, s), 3.63–3.70(2H, m), 3.86(1H, m), 4.01(1H, s), 4.12–4.28(2H, m), 6.55(2H, m), 7.03(3H, m), 7.51(2H, m); MS(ES$^+$)m/z 362(M+1, 100%). |
| 53 | 2'-CH$_3$ | 3'-F | H | $^1$H NMR(360MHz, CDCl$_3$)δ 1.65(1H, m), 2.10(3H, s), 2.24(1H, m), 3.12 (1H, m), 3.25(1H, m), 3.66(1H, t, J=7.9), 3.72(1H, m), 3.85(1H, m), 4.22 (1H, d, J=9.8), 4.36(1H, t, J=8.4), 4.50(1H, t, J=10.2), 6.20(1H, d, J=7.7), 6.78(1H, t, J=8.4), 6.87(1H, m), 7.04(2H, m), 7.65(2H, m), 9.97(1H brs), 10.59(1H, brs); MS(ES$^+$)m/z 346(M+1, 100%). |
| 54 | 3'-CH$_3$ | 5'-CH$_3$ | H | $^1$H NMR(360MHz, DMSO)δ 1.61(1H, m), 2.08(6H, s), 2.33(1H,m), 3.28 (2H, m), 3.52(2H, m), 3.87(1H, d, J=11.9), 4.16(1H, m), 4.32(1H, m), 4.74 (1H, s), 6.25(2H, s), 6.73(1H, s), 7.36(2H, t, J=8.9), 7.72(2H, m); MS(ES$^+$) m/z 342(M+1, 100%). |
| 55 | 2'-OCH$_3$ | 3'-OCH$_3$ | H | HCl salt $^1$H NMR(D$_2$O)δ 1.49(1H, dd, J=16.0, 10.0), 2.06(1H, dd, J=16.0, 10.0), 3.12(2H, m), 3.33(3H, s), 3.49(3H, s), 3.66(3H, m), 4.11(2H, m), 4.40 (1H, s), 5.90(1H, m), 6.57(2H, m), 6.91(2H, m), 7.30(2H, m); MS(ES$^+$)m/z 374(M+1, 100%). |
| 56 | 2'-C(O)N(CH$_2$CH$_3$)$_2$ | H | H | $^1$H NMR(250MHz, CDCl$_3$)δ 0.98–1.02(3H, m), 1.22–1.28(3H, m), 1.68–1.78 (1H, m), 2.01–2.32(2H, m), 3.02–3.23(4H, m), 3.40–3.46(1H, m), 3.40–3.70 (4H, m), 4.01(1H, s), 4.07–4.34(2H, m), 6.34–6.42(1H, m), 7.02–7.15(5H, m), 7.42–7.56(2H, m); MS(ES$^+$)m/z 413(M+1, 100%). |
| 57 | 2'-OCH(CH$_3$)$_2$ | 4'-F | 5'-F | $^1$H NMR(250MHz, CDCl$_3$)δ 1.05–1.18(6H, m), 1.89–2.11(2H, m), 2.39(1H, brs), 3.09(1H, dd, J=2.2, 12.2), 3.18(1H, ddd, J=3.5, 12, 12)3.67(1H, dd, J=5.9, 11.3), 3.91–3.93(1H, m), 4.02(1H, s), 4.07–4.35(4H, m), 6.42–6.46(1H, m), 6.80–6.91(1H, m), 6.98–7.05(2H, m), 7.44–7.50(2H, m); MS(ES$^+$)m/z 408 (M+1, 100%). |
| 58 | 2'-S(O)$_2$N(CH$_2$CH$_3$)$_2$ | H | H | $^1$H NMR(250MHz, CDCl$_3$)δ 1.11(6H, t, J=7.1), 1.69(1H, dd, J=7.5, 13), 2.31 (1H, dd, J=8.5, 13), 2.90–3.07(2H, m), 3.14–3.20(1H, m), 3.27(4H, dq, J=2.1, 7.2), 3.61–3.70(2H, m), 4.02(1H, s), 4.07–4.20(2H, m), 4.31–4.48(1H, m), 6.38–6.42(1H, m), 7.03(1H, dd, J=8.7), 7.12–7.16(2H, m), 7.42–7.52(2H, m), 7.69–7.76(1H, m); MS(ES$^+$)m/z 449 (M+1, 100%). |
| 59 | 2'-NH—(CH$_2$)$_3$-3' | | H | $^1$H NMR(360MHz, CDCl$_3$)δ 1.73–1.81(2H, m), 1.90(1H, bs), 2.08(1H, dd, J=12.8, 8.3), 2.67(2H, t, J=6.4), 2.88–2.95(1H, m), 3.01–3.10(2H, m), 3.18 (1H, dt, J=12.2, 3.6), 3.42(1H, bs), 3.57(1H, t, J=8.6), 3.64(1H, dd, J=11.6, 2.9), 3.74(1H, dd, J=8.5, 7.0), 4.02(1H, s), 4.17(1H, dt, J=11.8, 2.9), 4.25 (1H, t, J=8.6), 6.40(1H, t, J=7.4), 6.49(1H, dd, J=7.5, 1.3), 6.75(1H, dd, J=6.7, 0.7), 7.00(2H, m), 7.47(2H, m); MS(ES$^+$)m/z 369(M+1, 100%), 365 (12%). |
| 60 | 2'-F | 5'-F | H | $^1$H NMR(250MHz, CDCl$_3$)δ 1.72(1H, dd, J=12.8, 9), 2.22(1H, dd, J=10, 12.8), 3.04(1H, dd, J=2, 12), 3.20(1H, dt, J=3.6, 12), 3.58–3.71(2H, m), 3.80–3.89(1H, m), 4.00(1H, s), 4.20(1H, dt, J=3.6, 12), 4.33(1H, t, J=8), 6.19(1H, m), 6.70–6.89(2H, m), 6.95–7.0(2H, m), 7.43–7.52(2H, m); MS(ES$^+$)m/z 350 (M+1, 100%). |
| 61 | 2'-O—CH$_2$—O-3' | | H | HCl salt $^1$H NMR(d$_6$-DMSO)δ 1.65(1H, dd, J=11.0, 8.0), 2.41(1H, dd, J=11.0, 8.0), 3.46(2H, m), 3.55–3.69(2H, m), 3.97(1H, m), 4.28(1H, m), 4.44 (1H, m), 4.87(1H, s), 6.05(2H, s), 6.29(1H, d, J=1.0), 6.30(1H, dd, J=8.0, 1.0), 6.45(1H, m), 7.46(2H, m), 7.82(2H, m); MS(ES$^+$)m/z 358(M+1, 100%). |
| 62 | 2'-OCH$_3$ | 5'-CF$_3$ | H | $^1$H NMR(250MHz, CDCl$_3$)δ 1.82(1H, dd, J=10, 12), 2.11(1H, dd, J=8, 12), 3.04(1H, dd, J=2, 12), 3.19(1H, td, J=3.5, 12), 3.61(1H, t, J=8), 3.67(3H, s), 3.63–3.68(1H, m), 3.92(1H, me), 4.01(1H, s), 4.22(1H, dt, J=3.5, 12), 4.32 (1H, t, J=8), 6.77(1H, d, J=8), 6.90(1H, d, J=2), 7.00(2H, t, J=8.5), 7.36(1H, dd, J=2, 8.5), 7.45–7.53(2H, m); MS(ES$^+$)m/z 411(M+1, 100%). |
| 63 | 2'-OCH(CH$_3$)$_2$ | 4'-F | H | $^1$H NMR(360MHz, CDCl$_3$)δ 1.22(6H, m), 1.73(1H, m), 2.18(1H, m), 3.09 (1H, m), 3.20(1H, dt, J=3.8, 12.4), 3.53(1H, m), 3.67(1H, m), 3.89(1H, m), 4.07(1H, s), 4.23(1H, m), 4.39(2H, m), 6.38(1H, m), 6.49(2H, m), 7.03(2H, m), 7.46(2H, m); MS(ES$^+$)m/z 389(M+1, 100%). |

TABLE 1-continued

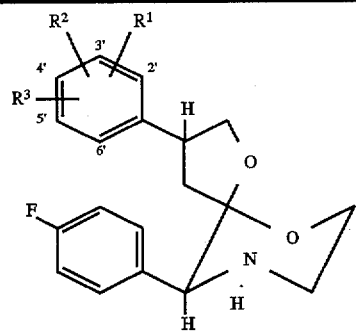

| Ex. No. | R¹ | R² | R³ | Data |
|---|---|---|---|---|
| 64 | 2'-O—(CH₂)₃-3' | | 5'-F | ¹H NMR(360MHz, DMSO)δ 1.71(1H, m), 1.80(1H, m), 2.18(1H, m), 2.65 (2H, t, J=6.4), 3.27(3H, m), 3.63(1H, t, J=7.8), 3.73(1H, m), 3.91(3H, m), 4.17(1H, m), 4.24(1H, t, J=8), 4.73(1H, s), 6.13(1H, dd, J=9.6, 3), 6.69(1H, dd, J=8.9, 3.1)7.31(2H, t, J=8.8), 7.67(2H, m); MS(ES⁺)m/z 388(M+1, 100%). |
| 65 | 2'-CH₂OH | H | H | ¹H NMR(250MHz, CDCl₃)δ 1.72(1H, dd, J=9.7, 12.8), 1.98(2H, brs), 2.20 (1H, dd, J=8.1, 12.8), 2.41–2.45(1H, m), 3.02(1H, dd, J=2.1, 12.2), 3.18(1H, ddd, J=3.6, 12.2, 12), 3.52–3.67(3H, m), 3.82–3.97(1H, m), 4.0(1H, s), 4.20 (1H, ddd, J=3, 11.6, 11.6), 4.32(1H, dd, J=8.2, 9.6), 6.47(1H, dd, J=1.5, 7.3), 6.93–7.26(5H, m), 7.50(2H, dd, J=5.6, 8.6); MS(ES⁺)m/z 344(M+1, 100%). |
| 66 | 2'-OCH(CH₃)₂ | 5-CF₃ | H | ¹H NMR(360MHz, CDCl₃)δ 1.24(6H, dd, J=6.0, 10.3), 1.74(1H, m), 2.21 (1H, m), 3.17(2H, m), 3.65(1H, m), 3.72(1H, m), 3.94(1H, m), 4.19(1H, s), 4.40–4.55(3H, m), 6.78(2H, m), 6.99(2H, m), 7.33(1H, m), 7.61(2H, m); MS (ES⁺)m/z 439(M+1, 100%). |
| 67 | 2'-CH₃ | 5'-F | H | ¹H NMR(360MHz, DMSO)δ 1.89(3H, s), 1.90(1H, m), 2.32(1H, m), 2.55 (1H, m), 3.31(2H, m), 3.83(1H, t, J=8.5), 3.93(1H, m), 4.11(1H, t, J=7.7), 4.23(1H, m), 4.70(1H, s), 6.90(1H, dt, J=8.4, J=2.8), 7.08(2H, m), 7.36(2H, t, J=8.9), 7.74(2H, m); MS(ES⁺)m/z 346(M+1, 100%). |
| 68 | 2'-OCH₂CHF₂ | 5'-F | H | ¹H NMR(360MHz, DMSO)δ 1.64(1H, m), 2.30(1H, m), 3.28(2H, m), 3.63 (1H, t, J=7.2), 3.83(1H, t, J=7.6), 3.90(1H, m), 4.21(3H, m), 4.32(1H, t, J=8.2), 4.76(1H, s), 6.28(1H, tt, J=54.5), 6.21(1H, dd, J=7.1), 6.95(2H, m), 7.28(2H, t, J=8.8), 7.67(2H, m); MS(ES⁺)m/z 412(M+1, 100%). |
| 69 | 2'-OCH₂CH₂N(CH₃)₂ | 5'-F | H | ¹H NMR(360MHz, CDCl₃)δ 1.69(1H, dd, J=12, 10), 2.15(1H, dd, J=8, 12), 2.37(6H, s), 2.74(2H, t, J=8), 3.03(1H, dd, J=2, 12), 3.17(1H, dt, J=3.5, 12), 3.40(2H, brs), 3.55(1H, dd, J=6.8, 15), 3.65(1H, dd, J=2, 12), 3.8–3.9(3H, m), 4.18(1H, dt, J=3.5, 12), 4.33(1H, t, J=8), 6.15(1H, dd, J=8.6, 2), 6.64–6.75(2H, m), 6.96–7.06(2H, m), 7.42–7.50(2H, m); MS(ES⁺)m/z 419(M+1, 50%), 210(M⁺/2). |
| 70 | 2'-OCH₂CH₂F | 5'-F | H | ¹H NMR(360MHz, DMSO)δ 1.66(1H, m), 2.86(1H, m), 3.15(2H, m), 3.62 (1H, t, J=8.15), 3.84(1H, t, J=8.4), 3.88(1H, d, J=14.8), 4.10(1H, m), 4.17 (2H, m), 4.32(1H, t, J=8.3), 4.57(1H, t, J=2.4), 4.70(1H, t, J=2.5), 4.75(1H, s), 6.23(1H, dd, J=9.9, 2.5), 6.93(2H, m), 7.28(2H, t, J=8.89), 7.66(2H, m); MS(ES⁺)m/z 394(M+1, 100%). |

TABLE 2

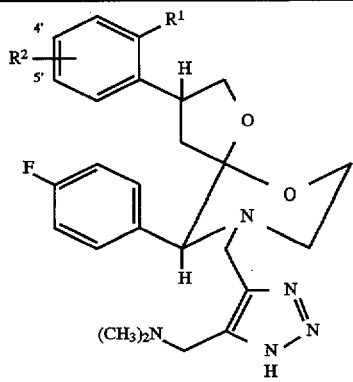

| Ex. No. | R¹ | R² | from Ex. No. | Data |
|---|---|---|---|---|
| 71 | OCH₃ | H | 10 | ¹H NMR(250MHz, CDCl₃)δ 1.84(1H, m), 2.10(1H, m), 2.21(6H, s), 2.54 (1H, m), 2.84(1H, d, J=11.3), 3.23(1H, d, J=14), 3.76–3.48(9H, m), 3.91 |

TABLE 2-continued

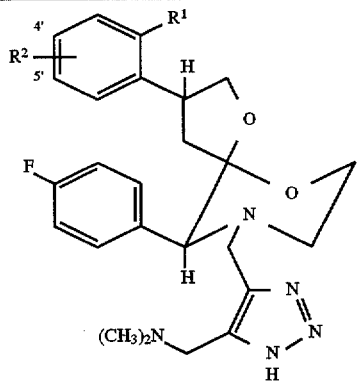

| Ex. No. | R¹ | R² | from Ex. No. | Data |
|---|---|---|---|---|
| | | | | (1H, m), 4.20(1H, m), 4.30(1H, t, J=8), 6.57(1H, dd, J=1.8, 8), 6.74(2H, m), 7.14–7.02(3H, m), 7.61(2H, brs); MS(ES⁺)m/z 482(M+1, 100%). |
| 72 | OCF₃ | H | 37 | ¹H NMR(250MHz, CDCl₃)δ 1.68(1H, m), 2.28(7H, m), 2.57(1H, m), 2.86 (1H, m), 3.30(1H, d, J=14), 3.51–3.71(6H, m), 3.93(1H, m), 4.14(1H, m), 4.30(1H, t, J=8.4), 6.33(1H, d, J=8.3), 6.95–7.10(5H, m), 7.61(2H, bs); MS(ES⁺)m/z 535(M+1, 100%). |
| 73 | OCH(CH₃)₂ | 5'-F | 45 | ¹H NMR(250MHz, CDCl₃)δ 1.14(1H, dd, J=6.1 and 8.6), 1.24(6H, dd, J=2.8 and 6.0), 1.64(1H, dd, J=9.8 and 9.8) 2.23(1H, dd, J=7.9 and 12.7), 2.08(6H, s), 3.56(1H, dd, J=7.8 and 7.8), 3.68–3.80(2H, m), 3.90–4.04(3H, m), 4.20–4.45(6H, m), 6.11(1H, dd, J=2.8 and 9.6), 6.63–6.74(2H, m), 7.11–7.20(2H, m), 7.58–7.82(2H, brm); MS(ES⁺)m/z 527(M+1, 100%). |
| 74 | OCH₃ | 5'-CH(CH₃)₂ | 47 | ¹H NMR(360MHz, CDCl₃)δ 1.10(6H, d, J=6.9), 1.85(1H, t, J=12.3), 2.09 (1H, m), 2.25(6H, s), 2.54(1H, dt, J=11.9, 3.5), 2.65(1H, m), 2.84(1H, m), 3.25(1H, d, J=13.9), 3.54(3H, m), 3.67(1H, d, J=13.9), 3.90(1H, m), 4.19 (1H, m), 4.29(1H, t, J=8.3), 6.44(1H, d, J=2.2), 6.66(1H, d, J=8.4), 6.95 (1H, dd, J=8.3, 2.2), 7.07(2H, t, J=8.7), 7.62(2H, brs); MS(ES⁺)m/z 524 (M+1, 100%). |
| 75 | OCH₂CH₃ | 5'-F | 48 | ¹H NMR(360MHz, CDCl₃)δ 1.32(3H, t, J=6.9), 1.72(1H, m), 2.17(1H, m), 2.30(6H, s), 2.56(1H, m), 2.81(1H, m), 3.26(1H, d, J=14.0), 3.48(1H, m), 3.60(5H, m), 3.89(3H, m), 4.17(1H, m), 4.33(1H, m), 6.12(1H, m), 6.64(1H, m), 6.73(1H, m), 7.04(2H, m), 7.6(2H, brs); MS(ES⁺)m/z 514 (M+1, 100%). |
| 76 | OCH₂CH₂CH₃ | H | 44 | ¹H NMR(500MHz, CDCl₃)δ 1.00(3H, t, J=7.4), 1.71(3H, m), 2.14(1H, m), 2.34(6H, s), 2.80(1H, d, J=10.4), 3.00(1H, dt, J=11.9, 3.6), 3.13(1H, d, J=17.3), 3.25(1H, d, J=17.3), 3.31(2H, s), 3.52(1H, t, J=8.1), 3.71(1H, s), 3.73(1H, d, J=2.91), 3.82(2H, t, J=6.5), 3.96(1H, m), 4.34(2H, m), 6.46(1H, d, J=6.4), 6.70(2H, m), 7.00(2H, t, J=8.6), 7.06(1H, m), 7.51 (1H, brs). |
| 77 | OCH₃ | 5'-CF₃ | 62 | ¹H NMR(360MHz, CDCl₃)δ 1.82(1H, t, J=10), 2.14(1H, dd, J=8, 12), 2.19(6H, s), 2.55(1H, td, J=3.6, 12), 2.85(1H, brd), 3.22(1H, d, J=14), 3.46(2H, s), 3.54(1H, t, J=8), 3.57(1H, s), 3.63(1H, brd), 3.68(3H, s), 3.90(1H, me), 4.18(1H, brt), 4.29(1H, t, J=8), 6.77(1H, d, J=8.5), 6.82 (1H, d, J=2), 7.05(2H, t, J=8.5), 7.36(1H dd, J=2, 8.5), 7.60(2H, m); MS (ES⁺)m/z 550(M+1, 100%). |
| 78 | OCH(CH₃)₂ | 4'-F | 63 | ¹H NMR(360MHz, CDCl₃)δ 1.24(6H, m), 1.71(1H, m), 2.11(1H, m), 2.20 (6H, s), 2.54(1H, dt, J=3.4, 11.9), 2.83(1H, d, J=11.5), 2.97(1H, d, J=11.9), 3.21(1H, d, J=13.9), 3.44(3H, m), 3.56(1H, s), 3.67(2H, m), 3.87 (1H, m), 4.22(1H, m), 4.30–4.43(2H, m), 6.36(2H, m), 6.45(1H, d, J=11.0), 7.04(2H, m), 7.59(2H, vbs); MS(ES⁺)m/z 527(M+1, 100%). |

EXAMPLE 79

(2S,3S,9S)-4-Aza-4-(2,3-dihydro-3-oxo-1,2,4-triazol-5-yl)methyl-1,7-dioxa-3-(4-fluorophenyl)-9-(3-(trifluoromethyl)phenyl)spiro[5.4]decane The title compound was obtained from the compound of Example 33 according to the method of Example 7.

¹H NMR (250 MHz, CDCl₃) δ1.75 (1H, m), 2.33 (1H, m), 2.56 (1H, m), 2.95 (2H, m), 3.46–3.68 (5H, m), 4.14 (1H, m), 4.40 (1H, m), 6.80 (1H, d, J=7.7), 6.96 (1H, s), 7.07 (2H, d, J=8.3), 7.26 (1H, m), 7.38 (1H, d), 7.58 (2H, vbs), 10.37 (1H, s), 10.90 (1H, s).

EXAMPLE 80

(2S,3S,9S)-4-Aza-1,7-dioxa-3-(4-fluorophenyl)-9-(2-naphthyl)-spiro[5.4]decane

The title compound was obtained from the compound of Description 14 and 2-naphthalene boronic acid according to the method of Example 9.

¹H NMR (250 MHz, CDCl₃) δ2.01 (1H, dd, J=12.8, 3.0), 2.29 (1H, dd, J=12.8, 8.0), 3.07 (1H, dd, J=12.2, 2.4), 3.21 (1H, dr, J=12.2,3.5), 3.71 (1H, dd, J=11.3, 3.0), 3.84 (1H, t, J=7.6), 3.93 (1H, s), 4.07 (1H, s), 4.27–4.41 (2H, m), 4.47 (1H, t, J=8.3), 6.85 (1H, d, J=7.0), 7.00 (2H, t, J=8.7), 7.20 (1H, t, J=7.7), 7.31–7.51 (4H, m), 7.62 (1H, d, J=8.2), 7.74–7.79 (2H, m); MS (ES⁺) m/z 364 (M+1, 100%).

EXAMPLE 81

(2S,3S,9S)-4-Aza-4-(2,3-dihydro-3-oxo-1,2,4-triazol-5-yl)methyl-1,7-dioxa-3-(4-fluorophenyl)-9-(2-naphthyl)spiro[5.4]decane The title compound was obtained from the compound of Example 80 according to the method of Example 7.

$^1$H NMR (360 MHz, d$_6$-DMSO) δ1.90 (1H, dd, J=12.9, 9.3), 2.30 (1H, dd, J=12.8, 8.4), 2.45 (1H, m), 2.80 (1H, dd, J=14.0, 7.7), 3.27 (1H, d. J=14.0), 3.58–3.69 (3H, m), 4.07–4.21 (2H, m), 4.31 (1H, t, J=8.3), 6.76 (1H, d, J=7.0), 7.13 (2H, t, J=8.8), 7.20 (1H, t, J=7.7), 7.30 (1H, t, J=7.7), 7.45 (1H, t, J=7.5), 7.59–7.70 (4H, m), 7.85 (1H, d, J=8.0), 11.22 (1H, s), 11.26 (1H, bs); MS (ES$^+$) m/z 461 (M+1, 100%).

EXAMPLE 82

(2S,3S,9S)-4-Aza-4-benzyl-1,7-dioxa-3-(4-fluorophenyl)-9-(2-thiomethylphenyl)spiro[5.4]decane a) (2S,3S,9S)-4-Aza-4-benzyl-1,7-dioxa-3-(4-fluorophenyl)-9-(2-thiomethylphenyl)spiro[5.4]dec-9-ene The title compound was obtained from the compound of Description 14 and 2-thiomethylphenylboronic acid according to the method of Example 9, step (a).

$^1$H NMR (360 MHz, CDCl$_3$) δ2.31 (3H, s), 2.38 (1H, dt, J=12.1, 3.6), 2.83 (2H, d, J=13.4), 3.62 (1H, s), 3.76 (2H, m), 4.33 (2H, m), 4.90 (1H, dd, J=13.1, 2.2), 5.91 (1H, s), 6.80 (1H, dd, J=7.7, 1.4), 6.96–7.05 (3H, m), 7.13–7.30 (7H, m), 7.58 (2H, br); MS (ES$^+$) m/z 448 (M+1, 100%).

b) (2S,3S,9S)-4-Aza-4-benzyl-yl-1,7-dioxa-3-(4-fluorophenyl)-9-(2-thiomethylphenyl)spiro[5.4]decane The compound of step (a) (266 mg, 0.59 mmol) in benzene:ethanol (1:1, 10 ml) was hydrogenated under one atmosphere of hydrogen for 18 hours with Wilkinson's catalyst (50 mg). The reaction mixture was filtered through hyflo™, concentrated to a crude oil (361 mg) and purified by flash silica gel chromatography eluting with 6:1 hexane-:ethyl acetate to yield the title compound as an oil (236 mg, 88%).

$^1$H NMR (360 MHz, CDCl$_3$) δ1.71 (1H, dd, J=12.9, 9.0), 2.13–2.27 (2H, m), 2.27 (3H, s), 2.67–2.76 (2H, m), 3.37 (1H, s), 3.41–3.52 (2H, m), 3.62 (1H, d J=13.2), 3.97 (1H, m), 4.09 (1H, dt, J=11.6, 2.2), 4.23 (1H, t, J=8.2), 6.20 (1H, dd, J=7.6, 1.0), 6.77 (1H, dt, J=7.0, 0.7), 6.88–7.18 (9H, m), 7.52 (2H, bs); MS (ES$^+$) m/z 450 (M+1, 100%).

EXAMPLE 83

(2S, 3S, 9S)-4-Aza-1,7-dioxa-9-(5-fluoro-2-methoxyphenyl)-3-(4-fluorophenyl)-4-(1,3-imidazol-4-ylmethyl)spiro [5.4]decane a) (2S,3S,9S)-4-Aza-1,7-dioxa-9-(5-fluoro-2-methoxyphenyl)-3-(4-fluorophenyl)-4-(N-p-toluenesulfonyl-1,3-imidazol-4-ylmethyl)spiro[5.4]decane The product of Example 41 (55 mg, 0.14 mmol) was dissolved in N,N-dimethylformamide (1 ml) and potassium carbonate added (58 mg, 0.42 mmol), followed by the product of Description 29 (69 mg, 0.2 mmol). The reaction mixture was stirred at room temperature for 12 hours, then diluted with water (10 ml) and extracted with ethyl acetate (3×30 ml). The combined organic phases were washed with brine, dried (MgSO$_4$), and concentrated in vacuo. Purification on flash silica, eluting with 5% methanol/dichloromethane gave the title compound. M/S ES$^+$=596 100%.

b) (2S,3S,9S)-4-Aza-1,7-dioxa-9-(5-fluoro-2-methoxyphenyl)-3-(4-fluorophenyl)-4-(1,3-imidazol-4-ylmethyl)spiro[5.4]decane The product of step (a) was dissolved in methanol/HCl (15 ml) and stirred at room temperature for 2 hours. The reaction was concentrated in vacuo, and the residue triturated with ether (×5) to yield the title compound as a pale yellow solid (45 mg) $^1$H NMR (360 MHz, d$_6$-DMSO) δ1.70 (1H, t, J=9.7), 2.16 (1H, t, J=12.8), 3.50 (2H, m), 3.72 (5H, m), 4.15 (2H, t, J=8.3), 6.18 (1H, m), 6.86 (2H, m), 7.11 (1H, d, J=7.75), 7.23 (2H, m), 7.46 (2H, d, J=8), 7.73 (2H, brs), 9.05 (1H, s). MS ES$^+$=442 100%.

Similarly prepared was

EXAMPLE 84

(2S,3S,9S)-4-Aza-1,7-dioxa-9-(5-fluoro-2-isopropoxyphenyl)-3-(4-fluorophenyl)-4-(1,3-imidazol-4-ylmethyl)spiro[5.4]decane From the product of Example 45 and the product of Description 29. MS (ES$^+$) m/z 470 (M+1, 100%).

EXAMPLE 85

(2S,3S,9S)-4-Aza-4-benzyl-9-(2,5-dimethoxyphenyl)-1,7-dioxa-3-(4-fluorophenyl)spiro [5.4]decane The product of Example 42 (200 mg), benzyl bromide (70 μl) and potassium carbonate (220 mg) were suspended in dimethylformamide (2 ml) and the mixture was heated to 60° C. for 2 hours. The mixture was cooled and diluted with water (30 ml) and ethyl acetate (20 ml). The organic layer was separated, washed with brine, dried (MgSO$_4$) and evaporated. The residue was purified by chromatography on silica using 10–20% ethyl acetate in hexane as eluant to give the title compound as a white solid.

$^1$H NMR (250 MHz, d$_6$-DMSO) δ1.88 (1H, t, J=10), 2.18 (1H, dd, J=8, 12.5), 2.32–2.41 (1H, m), 2.74–2.79 (1H, m), 2.93 (1H, d, J=12.5), 3.34 (1H, t, J=8), 3.61–3.68 (3H, m), 3.68 (3H, s), 3.69 (3H, s), 3.80–3.91 (1H, m), 4.08–4.17 (1H, m), 4.24 (1H, t, J=8), 6.16 (1H, d, J=3), 6.78 (1H, dd, J=3, 9), 6.90 (1H, d, J=9), 7.28–7.45 (7H, m), 7.77–7.83 (2H, m) MS (ES$^+$) m/z 464 (M+1, 100%).

EXAMPLE 86

(2S,3S,9S)-4-Aza-4-(carbonylmethylpyrrolidin-1-yl)-1,7-dioxa-3-(4-fluorophenyl)spiro[5.4]decane To a solution of the product of Example 10 (160 mg, 0.47 mmol), pyrrolidine acetic acid (92 mg, 0.56 mmol), and triethylamine (78 μl, 0.56 mmol) in dry dimethylformamide (3 ml) was added hydroxy benzotriazole trihydrate (HOBT; 65 mg, 0.49 mmol) then 1-(3-dimethylaminopropyl)-3-ethylcarbodiimide hydrochloride (WSCDI; 91 mg, 0.49 mmol). The reaction mixture was stirred at room temperature for 72 hours, diluted with water, then extracted with ethyl acetate (3×). The combined organic extracts were washed with brine (1×) then dried (MgSO$_4$) and concentrated to leave a brown oil. Purification on silica gel eluting with dichloromethane/methanol/ammonia (95:5:0.25 then 90:10:0.25) provided the title compound as a pale-yellow foam.

$^1$H NMR (250 MHz, CDCl$_3$) δ1.78 (4H, brs), 2.22 (1H, m), 2.60 (5H, m), 3.47–3.32 (3H, m), 4.07–3.74 (8H, m), 4.43 (1H, t, J=8), 5.56 (1H, brs), 6.85 (2H, m), 7.01 (3H, m), 7.20 (1H, m), 7.61 (2H, m); MS (ES$^+$) m/z 455 (M+1, 100%).

We claim:

1. A compound of the formula (I):

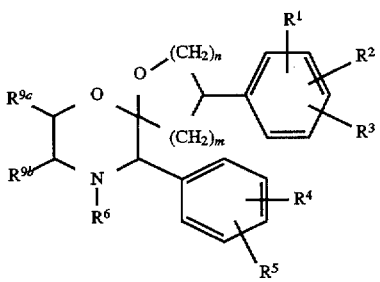

wherein

R$^1$ represents hydrogen, halogen, C$_6$alkyl, C$_{2-6}$alkenyl, C$_{2-6}$alkynyl, C$_{3-7}$cycloalkyl, C$_{3-7}$cycloalkylC$_{1-4}$alkyl, C$_{1-6}$alkoxy, fluoroC$_{1-6}$alkyl, fluoroC$_{1-6}$alkoxy, C$_{1-4}$alkyl substituted by a C$_{1-4}$alkoxy or hydroxy group, hydroxy, trimethylsilyl, nitro, CN, SR$^a$, SOR$^a$, SO$_2$R$^a$, COR$^a$, CO$_2$R$^a$, CONR$^a$R$^b$, NR$^a$R$^b$, SO$_2$NR$^a$R$^b$, or OC$_{1-4}$alkylNR$^a$R$^b$, where R$^a$ and R$^b$ are each independently hydrogen or C$_{1-4}$alkyl;

R$^2$ and R$^3$ each independently represent hydrogen, halogen, C$_{1-6}$alkyl, C$_{1-4}$alkoxy substituted by C$_{1-4}$alkoxy or trifluoromethyl;

or, where R$^1$ and R$^2$ are attached to adjacent carbon atoms, they may be joined such that, together the carbon atoms to which they are attached, there is formed a 5- or 6-membered ring optionally containing 1 or 2 heteroatoms selected from oxygen, sulfur or nitrogen, or 1 or 2 groups selected from S(O), S(O)$_2$ and NR$^a$, which ring may also contain 1 or 2 double bonds, where R$^a$ is as previously defined;

R$^4$ represents hydrogen, halogen, C$_{1-6}$alkyl, C$_{2-6}$alkenyl, C$_{2-6}$alkynyl, C$_{3-7}$cycloalkyl, C$_{3-7}$cycloyalkylC$_{1-4}$alkyl, C$_{1-6}$alkoxy, C$_{1-4}$alkyl substituted by a C$_{1-4}$alkoxy group, trifluoromethyl, nitro, CN, SR$^a$, SOR$^a$, SO$_2$R$^a$, COR$^a$, CO$_2$R$^a$, CONR$^a$R$^b$ where R$^a$ and R$^b$ are as previously defined;

R$^5$ represents hydrogen, halogen, C$_{1-6}$alkyl, C$_{1-6}$alkoxy substituted by C$_{1-4}$alkoxy or trifluoromethyl;

R$^6$ represents hydrogen, COR$^a$, CO$_2$R$^a$, COCONR$^a$R$^b$, COCO$_2$R$^a$, C$_{1-6}$alkyl optionally substituted by a group selected from (CO$_2$R$^a$, CONR$^a$R$^b$, hydroxy, CN, COR$^a$, NR$^a$R$^b$, C(NOH)NR$^a$R$^b$, CONHphenyl(C$_{1-4}$alkyl), COCO$_2$R$^a$, CONHNR$^a$R$^b$, C(S)NR$^a$R$^b$, CONR$^a$C$_{1-6}$alkylR$^{12}$, CONR$^{13}$C$_{2-6}$alkenyl, CONR$^{13}$C$_{2-6}$alkynyl, COCONR$^a$R$^b$, CONR$^a$C(NR$^b$)NR$^a$R$^b$, CONR$^a$heteroaryl, and phenyl optionally substituted by one, two or three substituents selected from C$_{1-6}$alkyl, C$_{1-6}$alkoxy, halogen and trifluoromethyl) or C$_{1-6}$alkyl, optionally substituted by oxo, substituted by a 5-membered or 6-membered heterocyclic ring containing 2 or 3 nitrogen atoms optionally substituted by =O or =S and optionally substituted by a group of the formula ZNR$^7$R$^8$ where Z is C$_{1-6}$alkylene or C$_{3-6}$cycloalkyl;

R$^7$ is hydrogen or C$_{1-4}$alkyl, C$_{3-7}$-cycloalkyl, C$_{3-7}$cycloalkylC$_{1-4}$alkyl, or C$_{2-4}$alkyl substituted by C$_{1-4}$alkoxy or hydroxyl;

R$^8$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy, hydroxyl or a 4, 5 or 6 membered heteroaliphatic ting containing one or two heteroatoms selected from N, O and S;

or R$^7$, R$^8$ and the nitrogen atom to which they are attached form a heteroaliphatic ring of 4 to 7 ring atoms, optionally substituted by one or two groups selected from hydroxy or C$_{1-4}$alkoxy optionally substituted by a C$_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is C$_{1-4}$alkyl optionally substituted by hydroxy or C$_{1-4}$alkoxy;

or R$^7$, R$^8$ and the nitrogen atom to which they are attached form a non-aromatic azabicyclic ring system of 6 to 12 ring atoms;

or Z, R$^7$ and the nitrogen atom to which they are attached form a heteroaliphatic ring to 4 to 7 ring atoms which may optionally contain an oxygen ring atom;

R$^{9a}$ and R$^{9b}$ each independently represent hydrogen or C$_{1-4}$alkyl, or R$^{9a}$ and R$^{9b}$ are joined so, together with the carbon atoms to which they are attached, there is formed a C$_{5-7}$ ring;

R$^{12}$ represents OR$^a$, CONR$^a$R$^b$ or heteroaryl;

R$^{13}$ represents H or C$_{1-6}$alkyl;

m is zero, 1, 2 or 3; and n is zero, 1, 2 or 3; with the proviso that the sum total of m and n is 2 or 3;

or a pharmaceutically acceptable salt thereof.

2. A compound as claimed in claim 1 of the formula (Ia) or a pharmaceutically acceptable salt thereof:

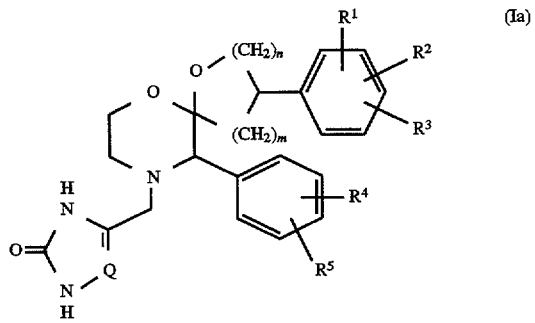

wherein R$^1$, R$^2$, R$^3$, R$^4$, R$^5$, m and n are as defined in claim 1 and Q$^1$ is CH, N or C—ZNR$^7$R$^8$ wherein Z, R$^7$ and R$^8$ are as defined in claim 1.

3. A compound as claimed in claim 1 of the formula (Ib) or a pharmaceutically acceptable salt thereof:

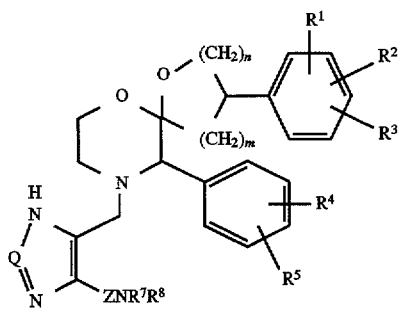

wherein $R^1$, $R^2$, $R^3$, $R^4$, $R^5$, m and n are defined in claim 1, $Q^2$ is CH or N and Z, $R^7$ and $R^8$ are as defined in claim 1.

4. A compound as claimed in claim 1 of the formula (Ic) or a pharmaceutically acceptable salt thereof:

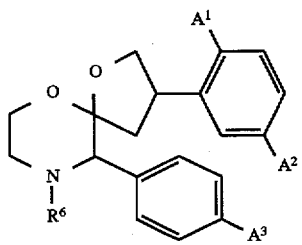

wherein $R^6$ is as defined in claim 1;
$A^1$ is $C_{1-4}$alkoxy;
$A^2$ is hydrogen, halogen, $C_{1-4}$alkyl or fluoro$C_{1-4}$alkyl; and
$A^3$ is hydrogen or halogen.

5. A compound as claimed in claim 1 of the formula (Id) or a pharmaceutically acceptable salt thereof

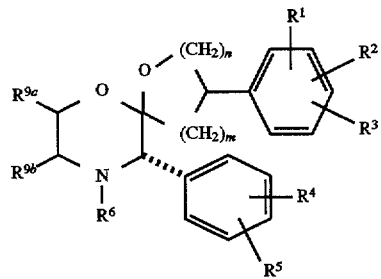

wherein $R^1$, $R^2$, $R^3$, $R^4$, $R^5$, $R^6$, $R^{9a}$, $R^{9b}$, m and n are as defined in claim 1.

6. A compound as claimed in claim 1 wherein $R^1$ is hydrogen, $C_{1-4}$alkyl, $C_{1-4}$alkoxy, halogen or $CF_3$.

7. A compound as claimed in claim 1 wherein $R^2$ is hydrogen, $C_{1-4}$alkyl, $C_{1-4}$alkoxy, halogen or $CF_3$.

8. A compound as claimed in claim 1 wherein $R^3$ is hydrogen, fluorine, chlorine or $CF_3$.

9. A compound as claimed in claim 1 wherein $R^4$ is hydrogen.

10. A compound as claimed in claim 1 wherein $R^5$ is hydrogen, fluorine, chlorine or $CF_3$.

11. A compound as claimed in claim 1 wherein n is 1.

12. A compound as claimed in claim 1 wherein m is 1 or 2.

13. A compound as claimed in claim 1 wherein $R^6$ is $C_{1-6}$alkyl substituted by a 5-membered heterocyclic ring containing 2 or 3 nitrogen atoms, which ring is optionally substituted by =O or =S and which ring is optionally substituted by a group of the formula $ZNR^7R^8$ where Z, $R^7$ and $R^8$ are as defined in claim 1.

14. A compound as claimed in claim 13 wherein the heterocyclic ring is selected from:

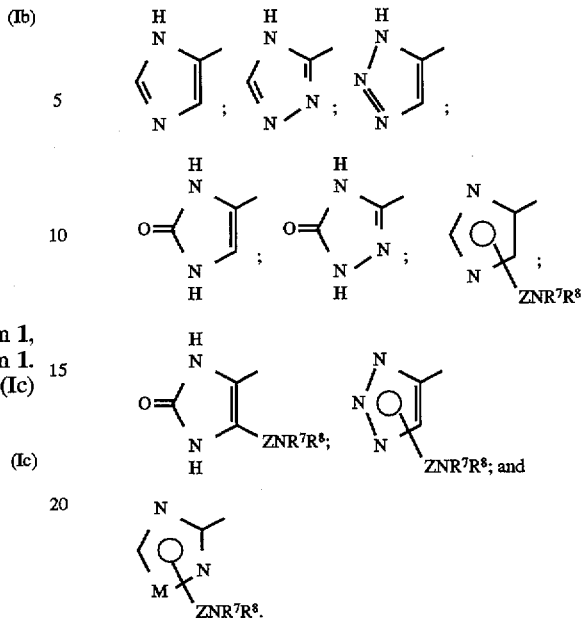

15. A compound as claimed in claim 14 wherein the heterocyclic ring is selected from:

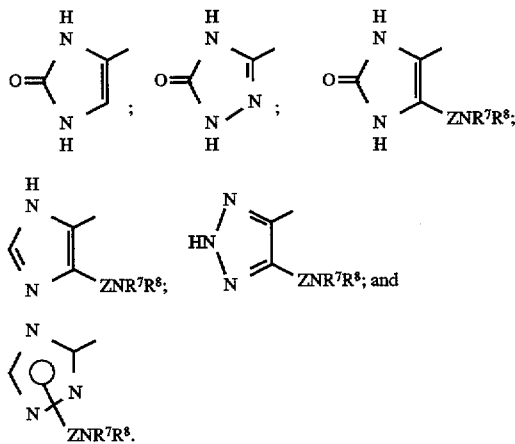

16. A compound as claimed in claim 1 wherein Z is $CH_2$.

17. A compound as claimed in claim 1 wherein $R^7$ is a $C_{1-4}$alkyl group or a $C_{2-4}$alkyl group substituted by a hydroxyl or $C_{1-2}$alkoxy group, $R^8$ is a $C_{1-4}$alkyl group or a $C_{1-4}$alkyl group substituted by a hydroxyl or $C_{1-2}$alkoxy group, or $R^7$ and $R^8$ are linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

18. A compound as claimed in claim 1 wherein Z is $CH_2$ and $NR^7R^8$ is dimethylamino, azetidinyl or pyrrolidino.

19. A compound selected from:

(2S,3S,9R)-4-aza-1,7-dioxa-3,9-diphenylspiro[5.5] undecane;

(2S,3S,9S)-4-aza-1,7-dioxa-3,9-diphenyl-spiro[5,5] undecane;

(2R,3S,9S)-4-aza-4-benzyl-1,7-dioxa-3,9-diphenyl-spiro [5.5]undecane;

(2R,3S,9R)-4-aza-4-benzyl-1,7-dioxa-3,9-diphenyl-spiro [5.5]undecane;

(2S,3S,9S)-4-aza-1,7-dioxa-3,9-diphenyl-spiro[5.5]undecane-4-ylmethyl)-2,4-dihydro-1,2,4-triazol-3-one;

4-aza-4-benzyl-1,7-dioxa-3,8-diphenyl-spiro[5.4]decane;

or a pharmaceutically acceptable salt thereof.

20. A compound selected from:

(2S,3S,9S)-4-aza-1,7-dioxa-3-(4-fluorophenyl)-9-phenylspiro[5.4]decane;

(2S,3S,9S)-4-aza-1,7-dioxa-3-(4-fluorophenyl)-9-(2-methoxyphenyl)spiro[5.4]decane;

(2R,3S,8R)-4-aza-4-benzyl-1,7-dioxa-3-(4-fluorophenyl)-8-phenyl-spiro[5.4]decane;

(2R,3S,8S)-4-aza-4-benzyl-1,7-dioxa-3-(4-fluorophenyl)-8-phenyl-spiro[5.4]decane;

(2R,3S,8R)-4-aza-1,7-dioxa-3-(4-fluorophenyl)-8-phenyl-spiro[5.4]decane;

(2R,3 S,9S)-4-aza-1,7-dioxa-3-(4-fluorophenyl)-8-phenyl-spiro [5.4]decane;

(2R,3S,8R)-4-aza-4-(2,3-dihydro-3-oxo-1,2,4-triazol-5-yl)methyl-1,7-dioxa-3-(4-fluorophenyl)-8-phenyl-spiro[5.4]decane;

(2R,3S,8S)-4-aza-4-(2,3-dihydro-3-oxo-1,2,4-triazol-5-yl)methyl-1,7-dioxa-3-(4-fluorophenyl)-8-phenyl-spiro[5.4]decane;

4-aza-4-benzyl-7-dioxa-5-phenyl-9-(2-trifluoromethylphenyl)spiro[5.5]undecane;

(2S,3S,9S)-4-aza-1,7-dioxa-3-(4-fluorophenyl)-9-(2-trifluoromethylphenyl)spiro[5.5]undecane;

(3R,3S,9S)-4-aza-1,7-dioxa-3-(4-fluorophenyl)-9-(2-trifluoromethylphenyl)spiro[5.5]undecane;

(2R,3S,9R)-4-aza-1,7-dioxa-3-(4-fluorophenyl)-9-(2-(trifluoromethyl)phenyl)spiro[5.5]undecane;

(2S,3S,9R)-4-aza-1,7-dioxa-3-(4-fluorophenyl)-9-(2-(trifluoromethyl)phenyl)spiro[5.5]undecane;

(2S,3S,9S)-4-aza-4-(5-(dimethylaminomethyl)-1,2,3-triazol-4-yl)methyl-1,7-dioxa-3-(4-fluorophenyl)-9-(2-(trifluoromethyl)phenyl)spiro[5.5]undecane;

4-aza-4-benzyl-1,7-dioxa-3-(4-fluorophenyl)-9-(3-(trifluoromethyl)phenyl)spiro[5.5]undecane;

(2R,3S,9S)-4-aza-1,7-dioxa-3-(4-fluorophenyl)-9-(3-(trifluoromethyl)phenyl)spiro[5.5]undecane;

(2R,3S,9R)-4-aza-1,7-dioxa-3-(4-fluorophenyl)-9-(3-(trifluoromethyl)phenyl)spiro[5.5]undecane;

(2S,3S,9R)-4-aza-1,7-dioxa-3-(4-fluorophenyl)-9-(3-(trifluoromethyl)phenyl)spiro[5.5]undecane;

(2S,3S,9S)-4-aza-1,7-dioxa-3-(4-fluorophenyl)-9-(3-(trifluoromethyl)phenyl)spiro[5.5]undecane;

(2S,3S,9S)-4-aza-4-(5-(dimethylaminomethyl)-1,2,3-triazol-4-yl)methyl-1,7-dioxa-3-(4-fluorophenyl)-9-(3-(trifluoromethyl)phenyl)spiro[5.5]undecane;

(2S,3S,9S)-4-aza-4-benzyl-7- dioxa-5-phenyl-9-(2-(trifluoromethoxy)phenyl-spiro[5.5]undecane;

(2S,3S,9S)-4-aza-1,7-dioxa-3-(4-fluorophenyl)-9-(2-(trifluoromethoxy)phenyl)spiro[5.5]undecane;

4-aza-1,7-dioxa-3-(4-fluorophenyl)-9-(2-(trifluoromethoxy)phenyl)spiro[5.5]undecane;

(2S,3S,9S)-4-aza-4-(5-(dimethylaminomethyl)-1,2,3-triazol-4-yl)methyl-1,7-dioxa-3-(4-fluorophenyl)-9-(2-(trifluoromethoxy)phenyl)spiro[5.5]un decane;

(2S,3S,9S)-4-aza-4-(2,3-dihydro-3-oxo-1,2,4-triazol-5-yl)methyl-1,7-dioxa-3-(4-fluorophenyl)-9-(3-(trifluoromethyl)phenyl)spiro[5.4]decane;

(2S,3S,9S)-4-aza-1,7-dioxa-3-(4-fluorophenyl)-9-(2-naphthyl)spiro[5.4]decane;

(2S,3S,9S)-4-aza-4-(2,3-dihydro-3-oxo-1,2,4-triazol-5-yl)methyl-1,7-dioxa-3-(4-fluorophenyl)-9-(2-naphthyl)spiro[5.4]decane;

(2S,3S,9S)-4-aza-4-benzyl-1,7-dioxa-3-(4-fluorophenyl)-9-(2-thiomethylphenyl)spiro [5.4]decane;

(2S,3S,9S)-4-aza-1,7-dioxa-9-(5-fluoro-2-methoxyphenyl)-3-(4-fluorophenyl)-4-(1,3-imidazol-4-ylmethyl)spiro[5.4]decane;

(2S,3S,9S)-4-aza-1,7-dioxa-9-(5-fluoro-2-isopropoxyphenyl)-3-(4-fluorophenyl)-4-(1,3-imidazol-4-ylmethyl)spiro [5.4]decane;

(2S,3S,9S)-4-aza-4-benzyl-9-(2,5-dimethoxyphenyl)-1,7-dioxa-3-(4-fluorophenyl)spiro[5.4]decane;

(2S,3S,9S)-4-aza-4-(carbonylmethylpyrrolidin-1-yl)-1,7-dioxa-3-(4-fluorophenyl)spiro[5.4]decane;

or a pharmaceutically acceptable salt thereof.

21. A compound of the formula

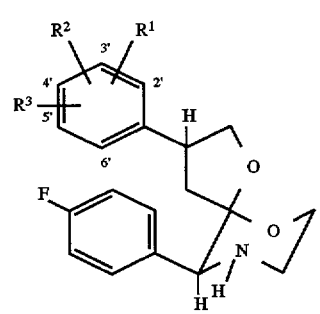

selected from the compounds in which $R^1$, $R^2$ and $R^3$ take the following definitions:

| Ex. No. | $R^1$ | $R^2$ | $R^3$ |
|---|---|---|---|
| 33 | 3'-$CF_3$ | H | H |
| 34 | 2'-$CF_3$ | H | H |
| 35 | 4'-$OCH_3$ | H | H |
| 36 | 2'-$CH_3$ | H | H |
| 37 | 2'-$OCF_3$ | H | H |
| 38 | 3'-$OCH_3$ | H | H |
| 39 | 3'-$NH_2$ | H | H |
| 40 | 3'-$OCH(CH_3)_2$ | H | H |
| 41 | 2'-$OCH_3$ | 5'-F | H |
| 42 | 2'-$OCH_3$ | 5'-$OCH_3$ | H |
| 43 | 2'-$OCH(CH_3)_2$ | H | H |
| 44 | 2'-$O(CH_2)_2CH_3$ | H | H |
| 45 | 2'-$OCH(CH_3)_2$ | 5'-F | H |
| 46 | 2'-$OCH(CH_3)_2$ | 5'-$CH(CH_3)_2$ | H |
| 47 | 2'-$OCH_3$ | 5'-$CH(CH_3)_2$ | H |
| 48 | 2'-$OCH_2CH_3$ | 5'-F | H |
| 49 | 2'-$OCH_3$ | 5'-$C(CH_3)_3$ | H |
| 50 | 2'-OH | H | H |
| 51 | 2'-$OCH_2CH_2$-3' | | H |
| 52 | 2'-$OCH_3$ | 6'-F | H |
| 53 | 2'-$CH_3$ | 3'-F | H |
| 54 | 3'-$CH_3$ | 5'-$CH_3$ | H |
| 55 | 2'-$OCH_3$ | 3'-$OCH_3$ | H |
| 56 | 2'-$C(O)N(CH_2CH_3)_2$ | H | H |
| 57 | 2'-$OCH(CH_3)_2$ | 4'-F | 5'-F |
| 58 | 2'-$S(O)_2N(CH_2CH_3)_2$ | H | H |
| 59 | 2'-NH–$(CH_2)_3$-3' | | H |
| 60 | 2'-F | 5'-F | H |
| 61 | 2'-O–$CH_2$–O-3' | | H |
| 62 | 2'-$OCH_3$ | 5'-$CF_3$ | H |
| 63 | 2'-$OCH(CH_3)_2$ | 4'-F | H |
| 64 | 2'-O–$(CH_2)_3$-3' | | 5'-F |
| 65 | 2'-$CH_2OH$ | H | H |
| 66 | 2'-$OCH(CH_3)_2$ | 5-$CF_3$ | H |
| 67 | 2'-$CH_3$ | 5'-F | H |
| 68 | 2'-$OCH_2CHF_2$ | 5'-F | H |
| 69 | 2'-$OCH_2CH_2N(CH_3)_2$ | 5'-F | H |
| 70 | 2'-$OCH_2CH_2F$ | 5'-F | H | or a pharmaceutically acceptable salt thereof.

22. A compound of the formula

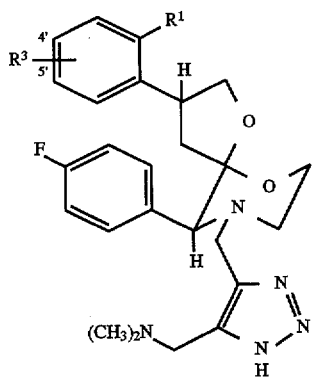

selected from the compounds in which $R^1$ and $R^2$ take the following definitions:

| Ex. No. | $R^1$ | $R^2$ |
|---|---|---|
| 71 | $OCH_3$ | H |
| 72 | $OCF_3$ | H |
| 73 | $OCH(CH_3)_2$ | 5'-F |
| 74 | $OCH_3$ | 5'-$CH(CH_3)_2$ |
| 75 | $OCH_2CH_3$ | 5'-F |
| 76 | $OCH_2CH_2CH_3$ | H |
| 77 | $OCH_3$ | 5'-$CF_3$ |
| 78 | $OCH(CH_3)_2$ | 4'-F | or a pharmaceutically acceptable salt thereof.

23. A pharmaceutical composition comprising a compound as claimed in claim 1 in association with a pharmaceutically acceptable carrier or excipient.

24. A method for the treatment or prevention of physiological disorders associated with an excess of tachykinins, which method comprises administration to a patient in need thereof of a tachykinin reducing amount of a compound according to claim 1, or a pharmaceutically acceptable salt thereof.

25. A method according to claim 24 for the treatment or prevention of pain or inflammation.

26. A method according to claim 24 for the treatment or prevention of migraine.

27. A method according to claim 24 for the treatment or prevention of emesis.

28. A process for the preparation of a compound as claimed in claim 1 which comprises:

(A), for a compound of formula (I) in which $R^6$ is other than H, reaction of a compound of formula (II)

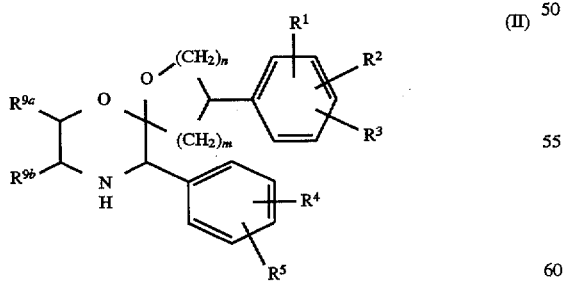

wherein $R^1, R^2, R^3, R^4, R^5, R^{9a}, R^{9b}$, m and n are as defined in claim 1 with a compound of formula (III):

where $R^{6a}$ is a group of the formula $R^6$ as defined in claim 1 or a precursor therefor and LG is a leaving group; and, if $R^{6a}$ is a precursor group, converting it to a group $R^6$; or (B), for a compound of formula (I) wherein $R^6$ represents a 1,2,3-triazol-4-ylmethyl group substituted by $CH_2NR^7R^8$, reaction of a compound of formula (IV)

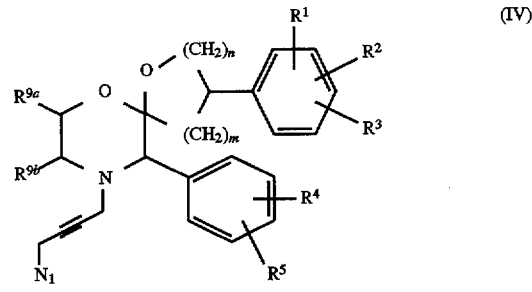

with an amine of formula $NHR^7R^8$; or (C), for a compound of formula (I) wherein $R^6$ represents a $C_{1-6}$alkyl group which is substituted by an unsubstituted or substituted 1,2,4-triazolyl group, reaction of an intermediate of formula (II) with a compound of formula (V)

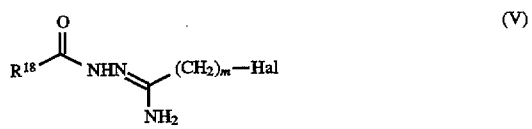

wherein Hal is a halogen atom, m is an integer from 1 to 6 and $R^{18}$ is H, $CONH_2$ or $OCH_3$, followed where necessary by conversion to a compound of formula (I); or (D), from a compound of formula (VI)

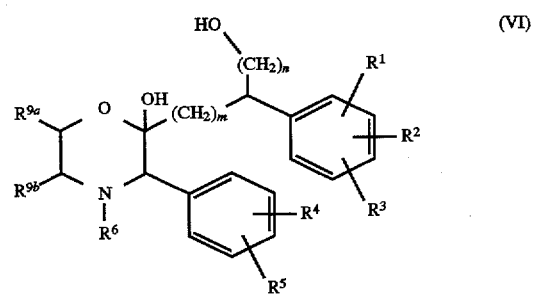

by an acid catalysed intramolecular cyclisation reaction; or (E), by interconversion from another compound of formula (I); or (F) for a compound of formula (I) in which n is 1 and m is 1, reduction of a compound of formula (XX)

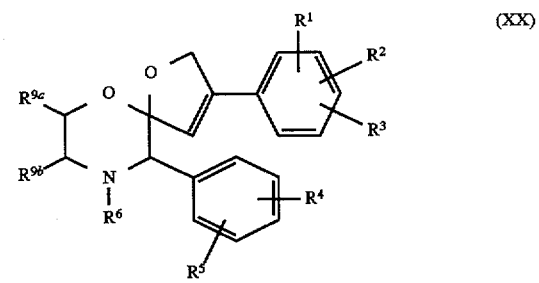

each process being followed, where necessary, by the removal of any protecting group where present;

and when the compound of formula (I) is obtained as a mixture of enantiomers or diastereoisomers, optionally resolving the mixture to obtain the desired enantiomer; and/or, if desired, converting the resulting compound of formula (I) or a salt thereof, into a pharmaceutically acceptable salt thereof.

* * * * *